United States Patent
Lehmann et al.

(10) Patent No.: US 10,866,250 B2
(45) Date of Patent: Dec. 15, 2020

(54) METHOD AND APPARATUS FOR MONITORING THE STATE OF HEALTH OF DAIRY COWS

(71) Applicant: Fraunhofer-Gesellschaft zur Foerderung der angewandten Forschung e.V., Müchen (DE)

(72) Inventors: Joerg Lehmann, Borsdorf (DE); Katharina Zoldan, Leipzig (DE)

(73) Assignee: Fraunhofer-Gesellschaft zur Foerderung der angewandten Forschung e. V, Munich (DE)

(*) Notice: Subject to any disclaimer, the term of this patent is extended or adjusted under 35 U.S.C. 154(b) by 0 days.

(21) Appl. No.: 15/580,983

(22) PCT Filed: Jun. 9, 2016

(86) PCT No.: PCT/EP2016/063109
§ 371 (c)(1),
(2) Date: Dec. 8, 2017

(87) PCT Pub. No.: WO2016/198501
PCT Pub. Date: Dec. 15, 2016

(65) Prior Publication Data
US 2018/0180632 A1   Jun. 28, 2018

(30) Foreign Application Priority Data
Jun. 10, 2015 (DE) .................. 10 2015 007 366

(51) Int. Cl.
*G01N 33/53* (2006.01)
*G01N 33/68* (2006.01)
*G01N 33/574* (2006.01)
*G01N 33/50* (2006.01)

(52) U.S. Cl.
CPC ..... *G01N 33/6893* (2013.01); *G01N 33/5091* (2013.01); *G01N 33/57488* (2013.01); *G01N 2333/4713* (2013.01); *G01N 2333/70535* (2013.01); *G01N 2800/7095* (2013.01)

(58) Field of Classification Search
None
See application file for complete search history.

(56) References Cited

U.S. PATENT DOCUMENTS

| | | | | |
|---|---|---|---|---|
| 7,172,872 B1* | 2/2007 | Eckersall | ............... | G01N 33/68 424/130.1 |
| 2006/0283269 A1* | 12/2006 | Anderson | ................. | A01J 5/04 73/863.31 |
| 2015/0045245 A1* | 2/2015 | Vanpoucke | ........ | G01N 33/6893 506/9 |
| 2015/0104816 A1* | 4/2015 | Noda | ............... | G01N 33/57438 435/7.92 |

FOREIGN PATENT DOCUMENTS

WO   01/27631 A1   4/2001

OTHER PUBLICATIONS

Groenlund et al., "Haptoglobin and serum amyloid A in milk from dairy cows with chronic sub-clinical mastitis", Veterinary Research, vol. 36, No. 2, (2005), pp. 191-198.
Kalmus et al. "Milk haptoglobin, milk amyloid A, and N-Acetyl-beta-D-glucosaminidase activity in bovines with naturally occurring clinical mastitis diagnosed with a quantitative PCR test", Journal of Dairy Science, vol. 96, No. 6 (2013), pages 3662-3670.
Boehmer et al., "The proteomic advantage: Label-free quantification of proteins expressed in bovine milk during experimentally induced coliform mastitis", Veterinary Immunology and Immunopathology, Veterinary Immunology and Immunopathology vol. 138, (2010), pp. 252-266.
Mansor, "Proteomic and Metabolic Studies on Milk during Bovine Mastitis", Glasgow Theses Service, available online at: http://theses.gla.ac.uk/3207/, (Feb. 2012), pp. 1-335.
Makimura et al., "Quantitative Determination of Bovine Serum Haptoglobin and Its Elevation in Some Inflammatory Diseases", Japanese Journal of Veterinary Science, vol. 44., (1982), pp. 15-21.
Ashour et al., "Use of a 96-Well Microplate Reader for Measuring Routine Enzyme Activities", Analytical Biochemistry vol. 166, (1987), pp. 353-360.
International Search Report and Written Opinion, International Patent Application No. PCT/EP2016/063109, dated Sep. 23, 2016, with English translation of Search Report (21 pages).

* cited by examiner

*Primary Examiner* — Gary Counts
(74) *Attorney, Agent, or Firm* — Hamre, Schumann, Mueller & Larson, P.C.

(57) ABSTRACT

Methods and apparatuses for monitoring the state of health of dairy cows, in particular of entire dairy herds are provided. The method is based on analysing the haptoglobin (HP) biomarker and part of the polymeric immunoglobulin receptor (PIGR), the secretory component (SC), in a milk sample. This allows diagnosis of mastitis or systemic diseases which occur outside the udder on the basis of the protein biomarker described here. This further allows regular monitoring of the general state of health of a dairy herd. Diagnostic methods, apparatuses, and diagnostic kits for carrying out these methods are included.

2 Claims, 14 Drawing Sheets

[Translation]
mRNA expression (% of PPIB/UXT)
HP – haptoglobin
MZ – milk cells
BL – leucocytes
control, n = 9
minor systemic disease, n = 6
serious systemic disease (+LMV), n = 6
mastitis (+systemic disease), n = 14
control, n = 20
systemic disease, n = 16
mastitis (+systemic disease), n = 7

[Translation]
mRNA expression (% of PPIB/UXT)
LTF - lactoferrin
MZ – milk cells
BL – leucocytes
control, n = 9
minor systemic disease, n = 6
serious systemic disease (+LMV), n = 6
mastitis (+systemic disease), n = 12
control, n = 5
systemic disease (+LMV), n = 4
mastitis, n = 4

[Translation]
mRNA expression (% of PPIB/UXT)
PIGR - polymeric immunoglobulin receptor
VEGF - Vascular Endothelial Growth Factor
MZ – milk cells
BL – leucocytes
control, n = 10/9
minor systemic disease, n = 6/3
serious systemic disease (+LMV), n = 6/5
mastitis (+systemic disease), n = 9

[Translation]
mRNA expression (% of PPIB/UXT)
ASB11
MZ – milk cells
BL – leucocytes
control, n = 9
minor systemic disease, n = 6
serious systemic disease (+LMV), n = 6
mastitis, n = 14
control, n = 15
systemic disease, n = 11
mastitis, n = 6

[Translation]
control (n = 4)
minor systemic disease (n = 4)
serious systemic disease (+LMV, n = 4)
mastitis (n = 4)

[Translation]
control (n = 14)
minor systemic disease (n = 10)
LMV (+ metabolic disorder, n = 6)
serious systemic disease (n = 3)
serious systemic disease +LMV (n = 9)
mastitis (n = 8)

[Translation]
control (n = 13)
minor systemic disease (n = 11)
LMV (+ metabolic disorder, n = 9)
serious systemic disease (+LMV, n = 12)
mastitis (n = 14)

[Translation]
Kontrolle — control
leichte system. Erkrank. — minor systemic disease
LMV + Stoffwechselerkrank. — LMV + metabolic disorder
schwere system. Erkrank. — serious systemic disease
schwere system. Erkrank. + LMV — serious systemic disease +LMV
Mastitis — mastitis
Mastitis + schwere system. Erkrank. — mastitis + serious systemic disease

[Translation]
Correlations for HP and LTF in milk and plasma
Concentration in milk [µg/mL]
Concentration in plasma [µg/mL]

1 ——— leichte system. Erkrank.
2 ········· LMV (+Stoffwechselerkrank.)
3 ═══ schwere system. Erkrank.
4 ········· schwere system. Erkrank. (+LMV)
5 ——— Mastitis

[Translation]
Sensitivity
Specificity
1 - minor systemic disease
2 - LMV (+ metabolic disorder)
3 - serious systemic disease
4 - serious systemic disease (+LMV)
5 - mastitis

[Translation]
Sensitivity
Specificity

[Translation]
Sensitivity
Specificity

1 —— HP
2 ······ PIGR
3 —— LTF
4 ······ VEGF

[Translation]
Sensitivity
Control vs. Disease
Specificity

METHOD AND APPARATUS FOR MONITORING THE STATE OF HEALTH OF DAIRY COWS

FIELD

The present invention relates to methods and apparatuses for monitoring the state of health of dairy cows, in particular of entire dairy herds.

SUMMARY

The present invention relates to methods and apparatuses for monitoring the state of health of dairy cows, in particular of entire dairy herds. The method is based on analysing the haptoglobin (HP) biomarker and part of the polymeric immunoglobulin receptor (PIGR), the secretory component (Secretory Component, SC), in a milk sample. In particular, the claimed method and apparatus of the invention make it possible to diagnose mastitis or systemic diseases which occur outside the udder on the basis of the protein biomarker described here. The invention therefore makes it possible to regularly monitor the general state of health of a dairy herd. The present invention relates to non-invasive diagnostic methods and to apparatuses and diagnostic kits for carrying out these methods.

DETAILED DESCRIPTION

Figure 1:
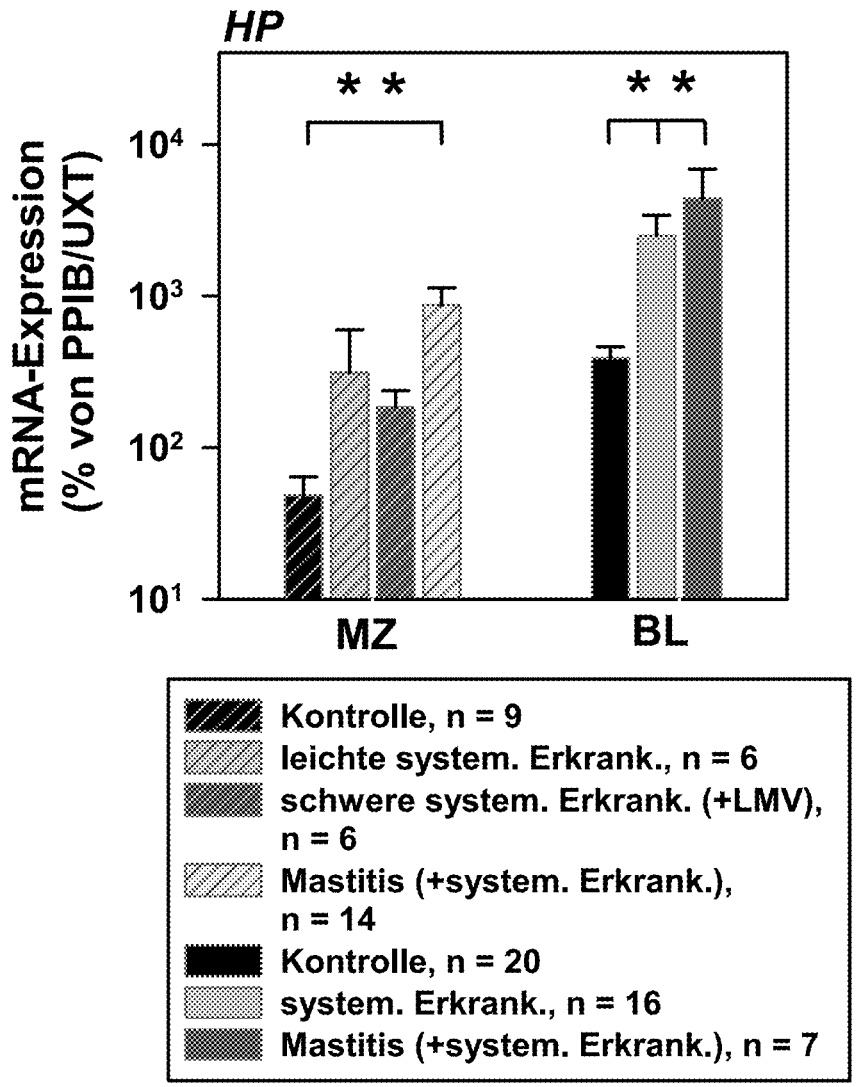
FIG. 1 shows mRNA expression of selected markers in milk cells and leucocytes from cows in various states of disease.
Figure 1:
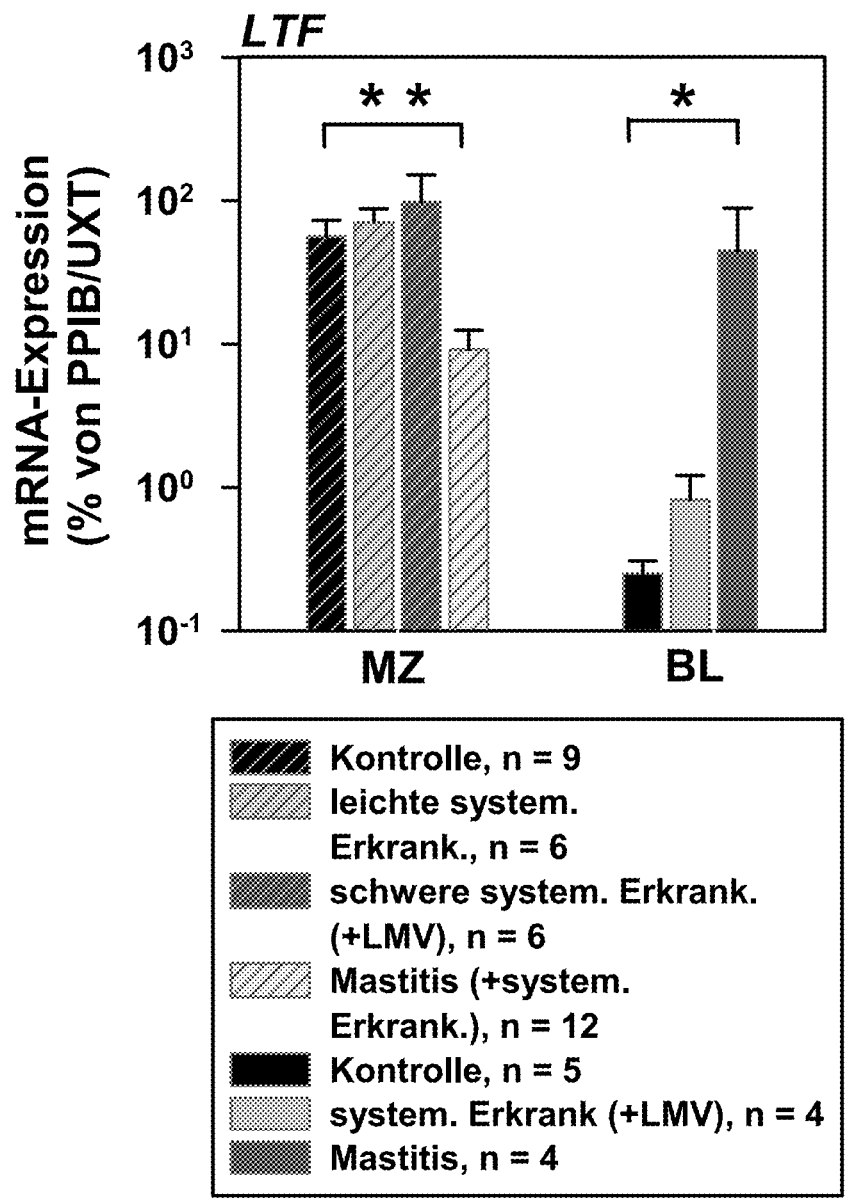
Figure 1:
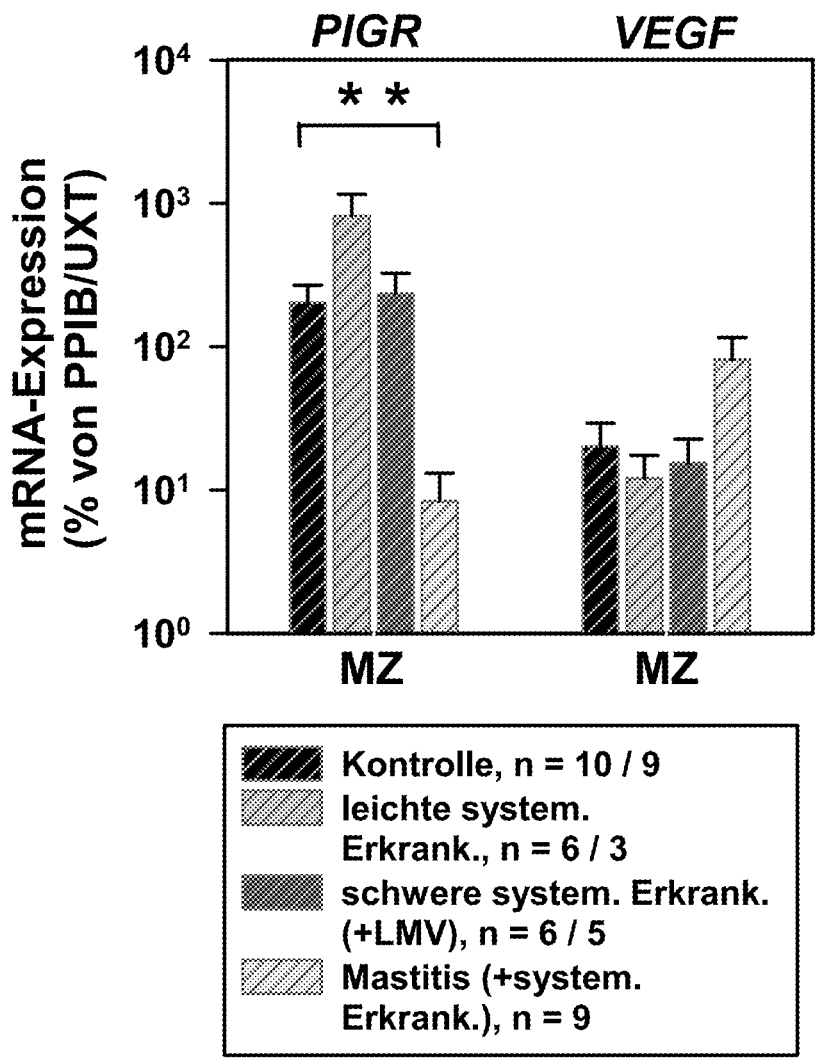
Figure 1:
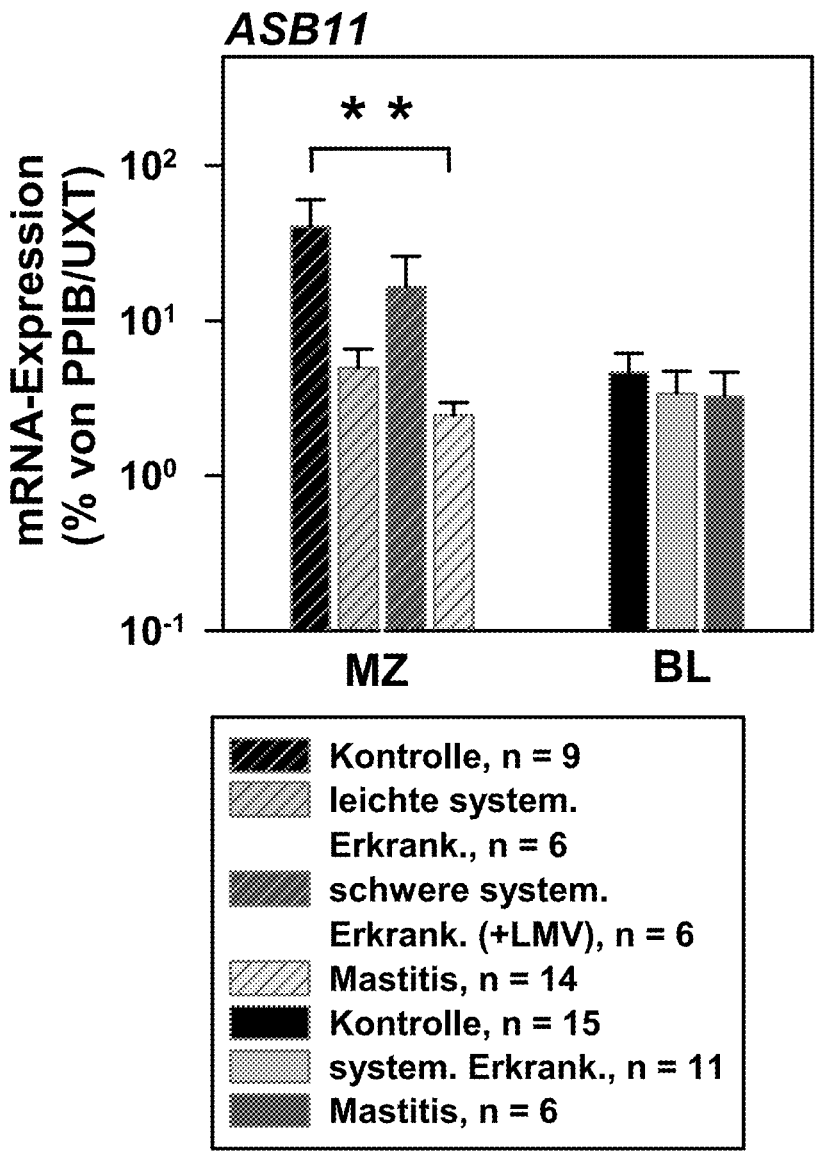

The latest technical methods are making it possible to cost-efficiently cultivate increasingly large dairy herds. Moreover, the use of automated milking systems can drastically reduce staffing requirements. However, this means that daily health checks can only be performed on the cows to a limited extent or not at all. Automated health monitoring is one possible solution to this problem. This can be done through the detection of certain health markers in the milk. Suitable markers include acute-phase proteins, such as HP, since their concentrations rise very quickly in the early phase of an immune response. HP measurements in milk are not currently done routinely in agriculture or in veterinary laboratory diagnostics.

Health monitoring after calving takes the form of a clinical examination 7-10 days after calving as well as a puerperal checkup (performed 20 to 28 days after calving) by the herd manager or trained barn staff. This involves assessing the general health, body temperature, lochia, milk production, as well as milk and ketones in urine, if applicable. Udder health is assessed daily by the milking staff at the milking stand. During the monthly milk production assessment, parameters such as cell count, uric acid content, and fat and protein content of the milk are collected in order to assess udder health and the metabolic condition of the individual animal and of the herd. A growing number of farms are able to determine the cell count from the automated milking system at each milking. Although there are approaches for routine detection of health parameters using various methods, they are only able to indicate the metabolic condition, a specific disease or the udder health of the animal.

Farm health monitoring is therefore highly subjective and labor-intensive. Existing solutions rely on the collection and evaluation of parameter combinations (milk conductivity, milk production, movement pattern, resting times, progesterone concentration, ketone bodies, lactate dehydrogenase, fat, protein, lactose and uric acid in milk) using the corresponding measurement techniques and multifunctional herd management programs, such as FullExpert (Lemmer-Fullwood). This enables identification of conspicuous animals (estrus, lameness, miscarriage, abomasal displacement, ketosis, mastitis). However, these systems are labor-intensive and expensive to procure. A veterinarian is consulted in the event of problematic results. The measurement of clinically relevant chemical, metabolic and endocrinological parameters in animal blood is done during routine checkups in veterinary laboratory diagnostics, but can only be performed by a veterinarian on selected, conspicuous or already diseased animals. Parameters used routinely in clinical chemistry can only provide an overall indication of a cow's condition in combination.

Approaches already exist for evaluating the health condition of a dairy cow more easily, quickly and objectively. This is done by measuring acute-phase proteins in the blood or milk. HP is the most frequently examined acute-phase protein in cattle. In the presence of mastitis, the HP concentration is significantly increased in milk as well. However, to date HP in milk has only been discussed as a potential indicator of mastitis.

SC is not an acute-phase protein, but rather forms part of a transmembrane receptor for polymeric immunoglobulins, PIGR, in secretory mucosal epithelial cells and also in the udder. During the binding of polymeric immunoglobulin (Ig)A or IgM, the antibody receptor complex is channeled from the lateral to the apical side of the epithelium via transcytosis. There, the receptor is cleaved enzymatically to release SC and IgA or IgM. This is how IgA is transported into the milk. During peripartum immunosuppression and early lactation, dairy cows are especially susceptible to infectious diseases that do not affect the udder (systemic diseases) such as uterine, hoof, or respiratory infections. Abomasal displacement is also not uncommon. Diagnostic examinations for these diseases are routinely done with animal blood, which requires veterinary assessment and treatment. Since a milk sample can be obtained with significantly less effort, it is in a farmer's economic interest to be able to detect systemic diseases based on this sample medium.

Health management teams at growing dairy farms are always looking for alternative solutions for herd monitoring. In practice, there are numerous parameters that enable the identification of conspicuous cows (estrus, lameness, miscarriage, abomasal displacement, ketosis, mastitis) based on daily, automated measurement at the farm. To date there is no validated milk biomarker to analyze the general state of health. Performing analysis on milk significantly simplifies the sampling process, which in turn makes it possible to perform the measurement at the farm. In particular, it should be emphasized that in contrast to taking a blood sample, the present solution does not require a veterinarian, which positively affects costs and is less of a hindrance to the overall agricultural production process. Accordingly, the problem that the present invention seeks to solve is to provide new approaches for the health management of dairy herds in which it is possible to perform simplified routine checks of large dairy herds that can be done without a veterinarian.

In a first aspect, the identified problem is solved by a non-invasive method for monitoring the state of health of a dairy cow, comprising the steps:
(a) Providing a milk sample from the dairy cow,
(b) Measuring the concentration of one or more biomarkers selected from among HP and PIGR (preferably SC) in the milk sample,
(c) Comparing the measured concentration from (b) with a reference value of the one or more measured biomarkers, wherein a deviation from the reference value indicates an unhealthy condition of the dairy cow.

In the context of the present invention, the determination of the PIGR marker in a milk sample preferably comprises the determination of the SC of the PIGR. It is therefore preferred that the measurement of the concentration of the biomarker PIGR in step (b) encompass measuring the concentration of the secretory component (SC) in the PIGR.

Preferably the non-invasive method is performed completely ex vivo or in vitro. In this regard, it should be emphasized that the biomarkers of the present invention are analyzed in a milk sample, meaning that the method can be performed without invasive sampling and therefore, without a veterinarian. This allows for expanding the present method to large herds of dairy cattle and to regular (monthly) tests, which is not cost-effective with, for example, analysis of biomarkers in a blood sample.

The terms "protein biomarker," "biomarker" and "marker" are used synonymously for the purposes of the present description. The terms preferably refer to the concentration of individual, or combinations of, biological molecules such as proteins, nucleic acids, carbohydrates, etc. In particular, the present disclosure pertains to proteins as biomarkers. Insofar as the disclosure relates to measuring biomarker concentrations, this is intended to include both a direct measurement of the concentration (number of protein molecules/volume or weight) as well as indirect measurement. In this way, degradation products of the protein markers according to the invention can also be measured, or alternatively, the biomarker concentrations can be inferred based on their biochemical characteristics. Enzymes can be determined through detection of their enzymatic activity, for example.

Insofar as is necessary, the method of the present invention can optionally include in step (b) the measurement of one or more additional biomarkers. The one or more additional biomarker(s) is preferably selected from the group comprising S100 calcium binding protein A9 (S100A9), interleukin (IL-) 18, tumor necrosis factor (TNF-) alpha, lactoferrin (LTF), and Vascular Endothelial Growth Factor (VEGF).

Especially preferred is a method wherein step (b) encompasses the measurement of a combination of two or more biomarkers and the combination of two or more biomarkers is selected from the combinations (i) HP and VEGF, (ii) HP and PIGR (preferably SC), (iii) HP and LTF, (iv) VEGF and PIGR (preferably SC), (v) LTF and PIGR (preferably SC), and (vi) LTF and VEGF. The combination of the markers HP and PIGR (preferably SC) has been shown to be especially advantageous and therefore represents a preferred embodiment of the present invention.

An additional optional and preferred further development of the present invention constitutes a method wherein step (b) encompasses the measurement of a combination of three or more biomarkers, namely HP, PIGR (preferably SC) and a third biomarker selected from the group comprising S100A9, IL-18, TNF-alpha, LTF, and VEGF. The specificity and sensitivity of the method can be further improved through measuring additional biomarkers.

A method described herein is preferred, wherein a deviation of the measured concentration of the biomarker from the reference value indicates mastitis or a systemic disease in the dairy cow, preferably a systemic disease that does not or not exclusively appear on the udder, such as for example minor systemic disease, minor systemic disease with abomasal displacement, serious systemic disease or combinations of these diseases. Preferably the measured deviation is an increased concentration of the biomarker in the sample of a sick cow compared to a healthy cow.

In one aspect, a systemic disease, preferably outside the udder, can be diagnosed based on the disclosed biomarkers [by using] the present invention. Alternatively, however, the invention also relates to the diagnosis of mastitis based on the disclosed biomarkers. For this aspect, there is a preferred embodiment of the invention in which mastitis in a dairy cow is diagnosed by determining a combination of the biomarkers HP and PIGR (preferably SC) or only based on the marker PIGR (preferably SC).

The term "reference value" is intended to be broadly interpreted here and to encompass a plurality of possible comparative values. A suitable reference value is selected based on the diagnostic objective. To identify sick animals, the reference value can be a value for the biomarker in a healthy cow. If the method is used to monitor the progression of a disease or to monitor a course of treatment for a sick cow, the reference value can also be a concentration of the biomarker in the milk of the monitored cow from an earlier point in time—especially before the treatment began. It is especially preferred, however, that the reference value be a threshold value (cut-off) wherein if the measured concentration of the biomarker exceeds the threshold value, it is determined that the cow is not in good health. Depending on how the cut-off is chosen, a non-healthy state can be determined based on a test value that is higher, or equal to and higher than, the cut-off. Additionally, a threshold value specific to the herd can be can be determined wherein a healthy dairy herd to be monitored is tested regularly for the biomarker and based on these values, a "healthy" reference value specific to the herd is determined. If a cow becomes conspicuous due to a higher concentration of the biomarker in the course of regular monitoring, it can be presumed that the cow is not in good health.

In preferred embodiments of the present invention, the threshold values (cut-offs) to distinguish healthy from sick animals can be chosen such that the corresponding biomarker has a specificity of 90% or higher, preferably 92%, more preferably 94% or higher, with a sensitivity of 50% or higher, preferably 60%, 70% or 80% or higher. For example, the threshold value for the marker HP can therefore be approximately 0.4 µg/ml, preferably approximately 0.5 µg/ml and most preferably approximately 0.58 µg/ml. For example, the threshold value for the marker PIGR (preferably SC) can be approximately 5 µg/ml, preferably approximately 8 µg/ml and most preferably approximately 8.2 µg/ml. The threshold value for the marker LTF can be, for example, approximately 80 µg/ml, preferably approximately 100 µg/ml and most preferably approximately 120 µg/ml. The value for the marker VEGF can be approximately 7 µg/ml, preferably approximately 9 µg/ml and most preferably approximately 9.5 µg/ml, for example. The term "approximately" in connection with numerical information preferably refers to a deviation of +/−20% of the specified value, more preferably a deviation of +/−15%, +/−10%, and most preferably +/−5%.

The biomarkers and biomarker combinations described herein have been found to be especially advantageous for diagnosing systemic diseases. In some embodiments, the method is therefore not used to diagnose mastitis, in particular, but rather only to detect systemic diseases. In this regard, with some embodiments, the diseases can be detected at an early stage.

As mentioned above, the non-invasive method according to the invention is suitable for monitoring a treatment of a dairy cow, wherein a reduction in the biomarker concentration during or following a treatment indicates a successful treatment. Since the increase of the biomarkers in the milk described here correlates to a deterioration of a dairy cow's state of health, the method can also be used to monitor the success of treatments for individual sick animals. In this regard, the reference value with which a measured concentration of the biomarker(s) according to the invention in the milk sample is compared, is [equivalent to], for example, a concentration of the biomarker(s) in the milk of the same cow at an earlier point in time, especially at the beginning of the treatment.

It is especially preferred for the present invention that in step (b) both HP as well as PIGR (preferably SC) be measured.

In some embodiments it is preferred that the concentration of the biomarker HP be determined in an undiluted milk sample. In other embodiments the milk sample is a milk sample to which preservatives have been added (e.g., during the milk production test).

The method of the present invention can be used especially on a routine basis for monitoring a dairy cow or a dairy herd. It is therefore preferred that the non-invasive method be performed regularly, preferably monthly, more preferably weekly, and even more preferably several times per week, up to daily.

To carry out the method according to the invention, the milk sample from the dairy cow that is to be analyzed is preferably taken during a milking (non-invasively). With fully automated milking systems, the milk sample from a dairy cow can be (automatically) diverted directly. The milk sample obtained in this manner is then used for the method according to the invention described here.

To measure the concentration of the biomarkers, the present invention can refer back to various technical methods with which one skilled in the art is familiar. In particular, the present disclosure should not be regarded as limited to individual analysis methods. The determination of the concentration of biomarkers in a milk sample can encompass measuring the concentration biochemically by means of a method selected from among Sodium Dodecyl Sulfate Polyacrylamide Gel Electrophoresis (SDS-PAGE), Fast Protein Liquid Chromatography (FPLC), and High Performance Liquid Chromatography (HPLC), or measuring the concentration immunologically by means of a method selected from among Enzyme-linked Immunosorbent Assay (ELISA), Enzyme immunoassay (EIA), Fluorescence immunoassay (FIA), Chemiluminescence immunoassay (CIA), Radio immunoassay (RIA), Western blot, and peptide arrays, or encompass measuring the concentration spectrometrically by means of a method selected from among Surface Plasma Resonance (SPR), Matrix-assisted Laser Desorption/Ionization (MALDI) or Electrospray Ionization (ESI). Immunological methods, especially by means of monoclonal (preferred) or polyclonal antibodies, such as in an ELISA, are especially preferred.

The described method is intended to be used, in particular, to monitor the state of health of one or more dairy cows. It is therefore intended in several embodiments that the method be used to determine an unhealthy condition in a dairy cow. In this embodiment, it is not absolutely necessary for a specific diagnosis to be made by the present invention of the dairy cow categorized as unhealthy. Rather, the disease from which the identified unhealthy dairy cow is suffering can be determined by performing additional subsequent diagnostic procedures. In this embodiment, the method of the present disclosure focuses on detecting conspicuous animals as early as possible through regular assessments according to the present invention. When an unhealthy condition is determined to exist, a veterinarian can be subsequently consulted to establish a specific diagnosis.

In several embodiments, the present disclosure concerns a non-invasive method to monitor the state of health of a dairy herd at a dairy farm, comprising regular performance of a method to monitor the state of health of one or more, preferably all, dairy cows in the dairy cattle herd, according to the non-invasive method for monitoring the state of health of a dairy cow described here.

A dairy cattle herd is understood to mean a group of dairy cattle within a dairy farm of preferably two or more animals, more preferably 5 or more animals, 10 animals, 15 animals, 20 animals, 50 animals or more. The present invention is especially helpful for monitoring dairy cattle herds with more than 10 animals.

The present problem is additionally solved in another aspect by a non-invasive system and/or apparatus for monitoring the state of health of a dairy cow, comprising:
(a) Means to take a milk sample from the dairy cow;
(b) Means to measure the concentration of one or more biomarkers selected from among HP and/or PIGR (preferably SC) in the milk sample;
(c) Means to compare the measured concentration from (b) with a reference value of the measured biomarker, wherein a deviation of the measured concentration from the reference value indicates an unhealthy condition in the dairy cow.

In several embodiments, the non-invasive system and/or apparatus can comprise additional means to store data and/or means to optically display data, such as a screen.

In several embodiments, the non-invasive system and/or apparatus comprises means for information output. When an unhealthy condition is detected in a cow, the means for information output are suitable to communicate this message. For example, upon detection of an unhealthy condition in a dairy cow, a visual or acoustic alarm can be triggered. Preferably, one or more messages about the identity of the identified unhealthy dairy cow are provided.

Preferably the system and/or apparatus described here is connected to a milking system and comprises means that transfer a milk sample taken from the dairy cow from the milking system to the means provided for receiving a milk sample. One skilled in the art is familiar with automated milking systems that enable milk samples to be taken.

The non-invasive system and/or apparatus according to the present invention preferably comprises additional means to measure one or more additional biomarkers selected from the group comprising S100A9, IL-18, TNF-alpha, LTF, and VEGF. More preferably the system and/or apparatus comprises means to measure the concentration of the biomarker(s) HP and/or PIGR (preferably SC) in the milk sample.

In several embodiments, the means to measure the concentration of a biomarker are selected from among means to perform one of these methods: SDS-PAGE, FPLC, and HPLC, or EIA, FIA, CIA, RIA, Western Blot, and peptide arrays, or SPR, MALDI or ESI. In particular, it is preferred that the non-invasive system and/or apparatus comprise antibodies to measure the concentration of the specified biomarkers.

The non-invasive system and/or apparatus according to the present invention is therefore suitable for performing one of the methods described here.

The problem that the invention seeks to solve is additionally solved by a diagnostic kit for monitoring the state of health of a dairy cow, comprising means to determine the concentration of one or more biomarkers selected from HP and/or PIGR (preferably SC) in a milk sample.

In several embodiments, the diagnostic kit according to the invention comprises means to perform a method selected from among SDS-PAGE, FPLC, and HPLC, or EIA, FIA, CIA, RIA, Western blot, and peptide arrays, or SPR, MALDI or ESI. In several embodiments, the kit comprises antibodies for detection or measurement of the concentration of one of the specified biomarkers. In particular, the diagnostic kit is suitable for performing one of the methods described here to monitor the state of health of dairy cattle.

Below, the present invention is further described on the basis of non-restricting examples.

The figures show:

FIG. 1: mRNA expression of selected markers in milk cells (MZ) and leucocytes (BL) from cows in various states of disease. The concentration of the markers was determined with qPCR and is given as a percentage of the expression of the reference gene cyclophilin B (PPIB) and ubiquitously expressed transcript (UXT). system: systemic; Erkrank: disease; MZ: milk cells; BL: leucocytes; * $0.05>p>0.01$, and ** p 0.01.

Figure 2:
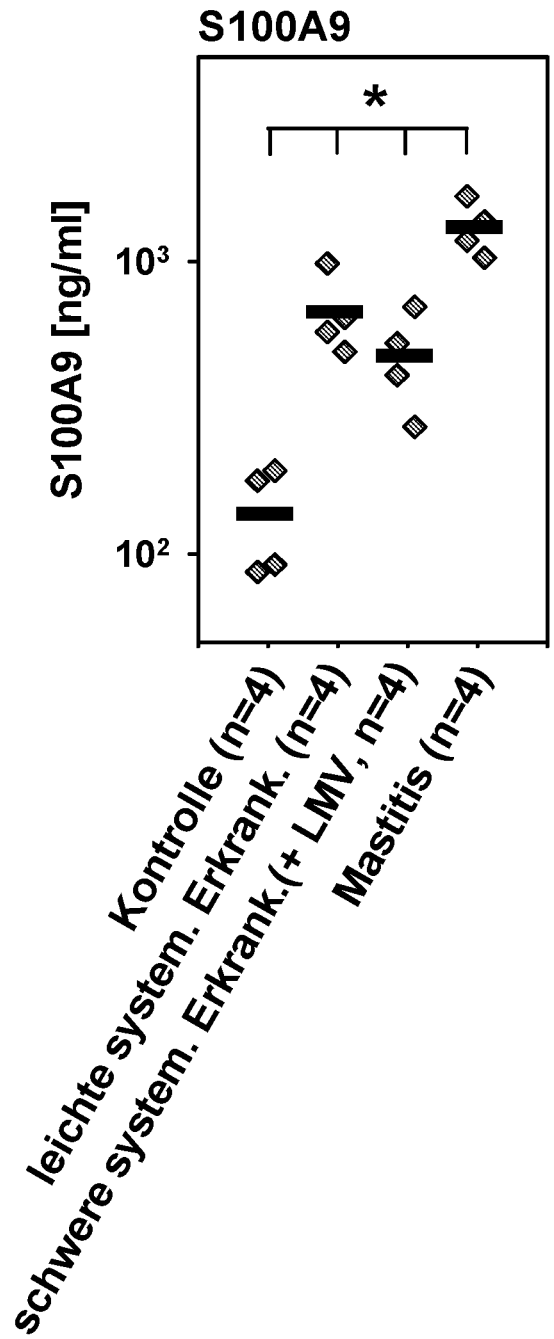
FIG. 2 shows concentrations of potential protein biomarkers in milk.
Figure 2:
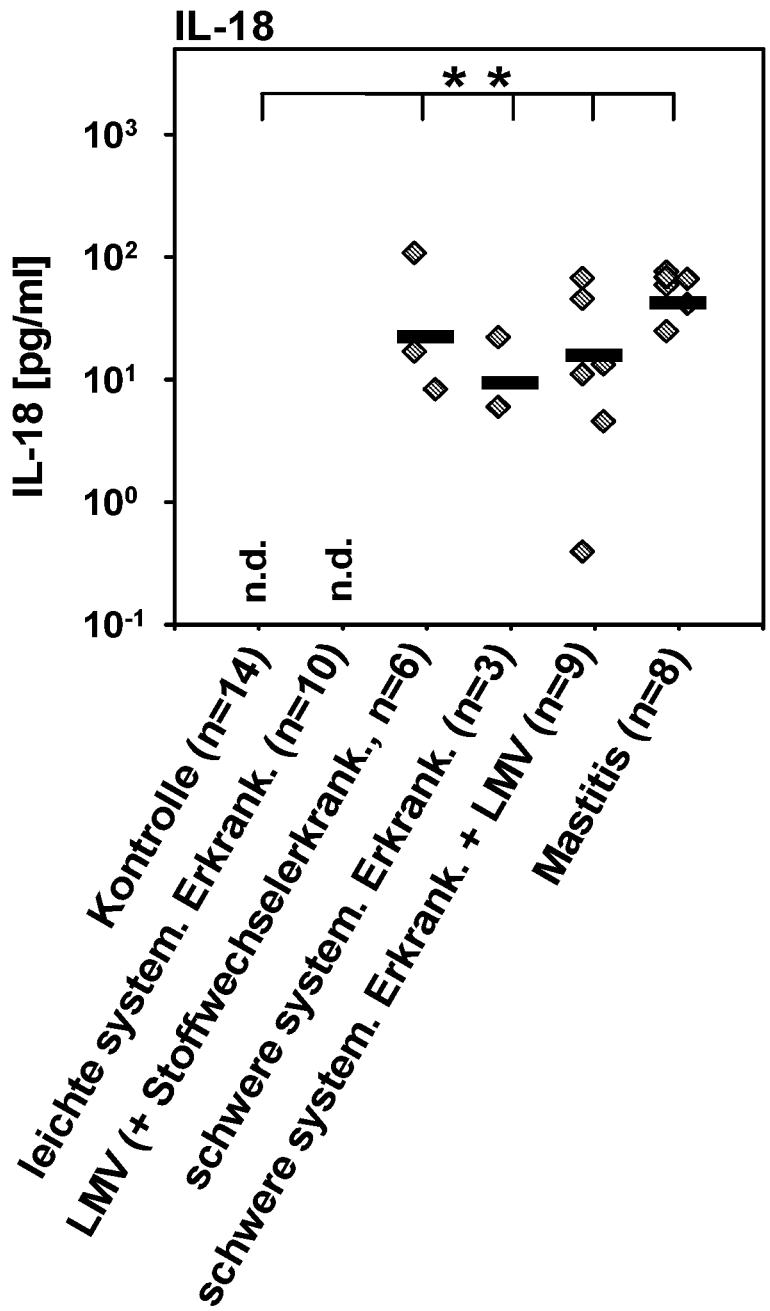
Figure 2:
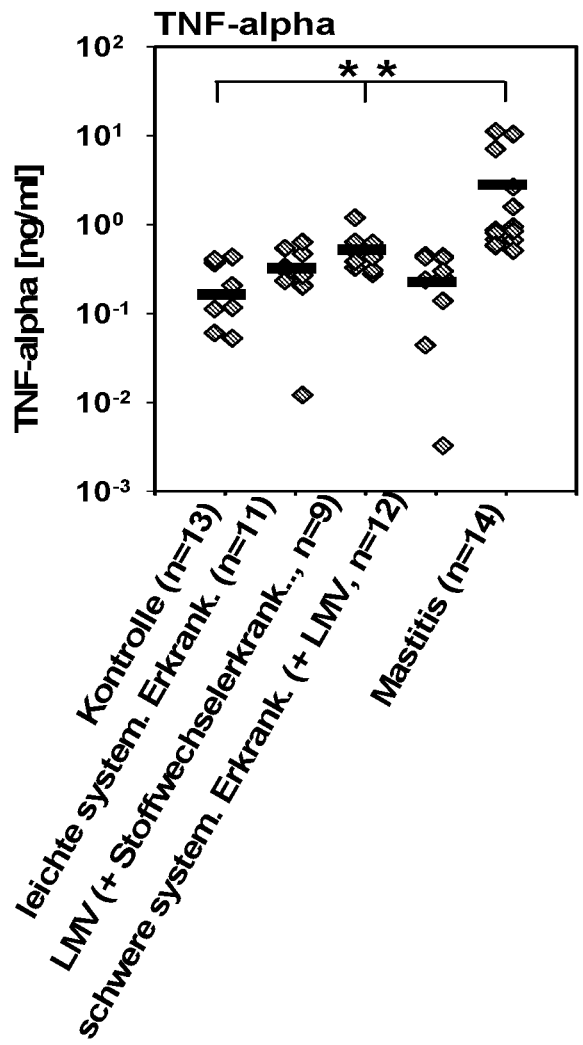
Figure 2:
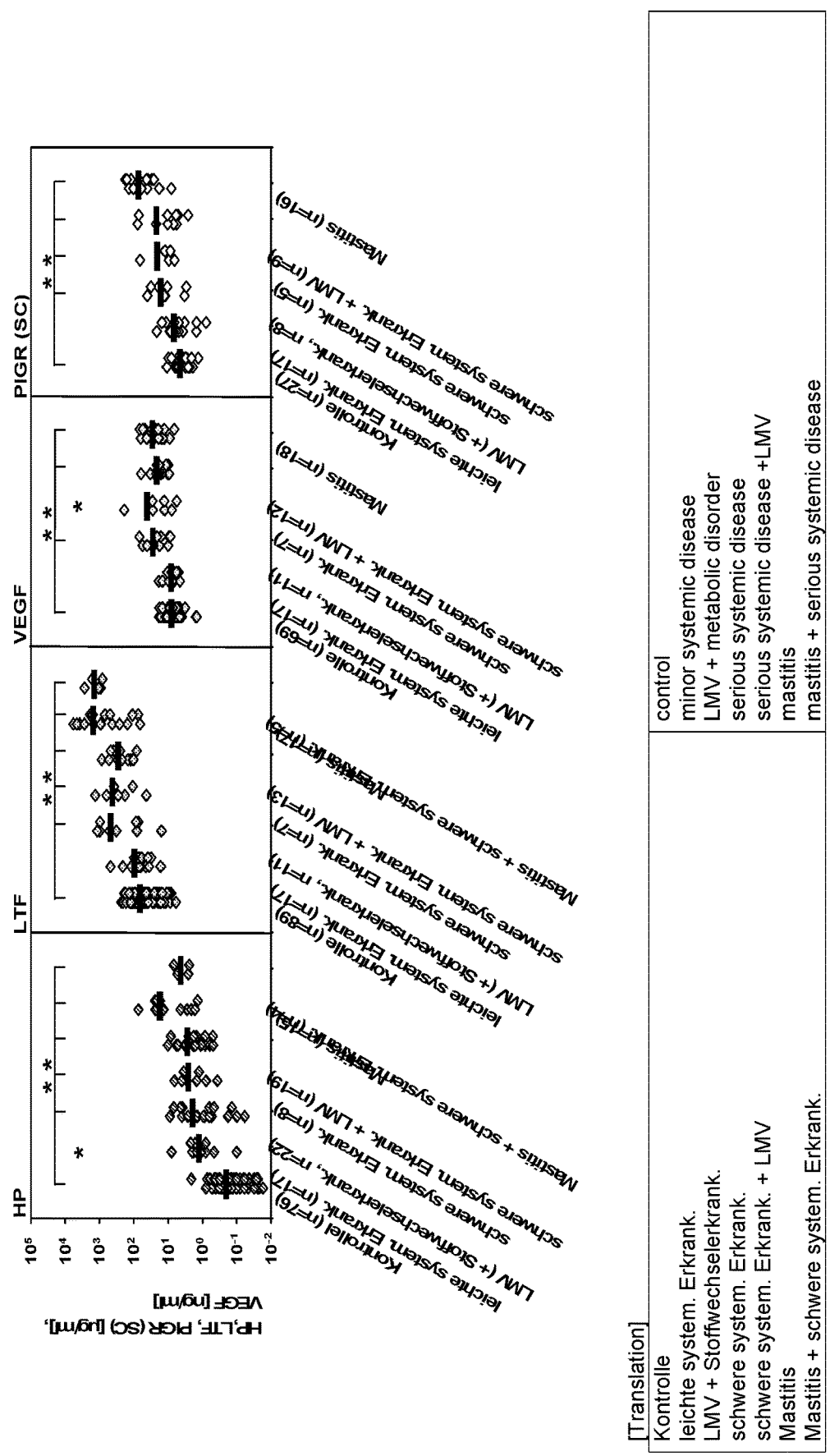

FIG. 2: Concentrations of potential protein biomarkers in milk. The concentrations were determined using commercially available ELISA kits. n.d.=non-detectable; system: systemic; Erkrank: disease; * $0.05>p>0.01$, and ** $p \leq 0.01$.

Figure 3:
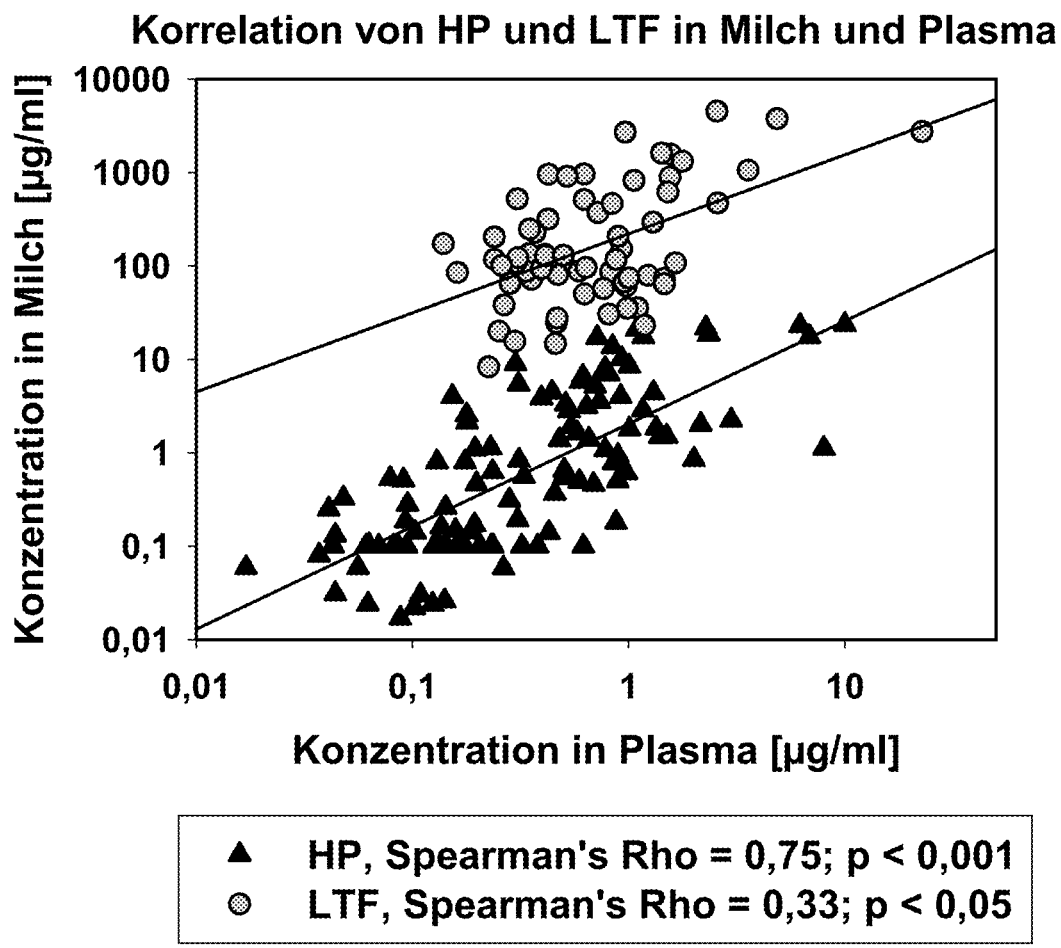
FIG. 3 shows concentration correlations for the biomarkers haptoglobin (HP) and lactoferrin (LTF) in milk and plasma.

FIG. 3: Concentration correlations for the biomarkers HP and LTF in milk and plasma. The concentrations were determined using commercially available ELISA kits. Positive correlations are indicated by the regression lines.

FIG. 4: ROC curves from selected milk biomarkers. A: ROC analysis of the individual markers in various states of disease. B: Summarized ROC analysis of all sick animals. system: systemic; Erkrank: disease

EXAMPLES

Material and Methods:

Quantification of Protein Biomarkers in Milk and Plasma

Selected proteins in milk and plasma were quantified using commercially available ELISA kits. All HP measurements were done based on undiluted samples since this is sufficient to detect fluctuations of the HP marker at various stages of disease. Precoated plates were incubated with 100 μl of sample (30 min, room temperature (RT)). Purified HP (LeeBioSolutions, St. Louis, Mo., USA) was used as the standard in a range from 8 to 0.125 μg/ml. The plate was washed 3 times in assay wash buffer, then incubated with 100 μl of 1:40 diluted peroxidase-conjugated anti-HP antibodies (30 min, RT). After 3 washings, 100 μL of ready-made tetramethylbenzidine substrate solution (Moss Inc., Pasadena, Md., USA) was added, and incubated for 10 to 30 minutes at RT. The reaction was stopped with 50 μl 9.9% $H_3PO_4$.

PIGR (SC) was quantified with an ELISA kit to detect bovine PIGR (Life Science USCN Inc.) according to the manufacturer's information. In each case, milk was diluted at a ratio of 1:300 to 1:1,000 for the control samples and 1:5,000 to 1:10,0000 for samples from sick cows. Plasma samples were diluted 1:100,000.

Statistical Analysis

Analysis of the differences between the groups was performed by means of Spearman rank correlations, Receiver Operating Characteristic (ROC) analysis and visualization of the results using SigmaPlot11 Software (Systat Software, Erkrath, Germany). To avoid undesired statistical tendencies, animal samples were randomly selected for analysis with quantitative real-time RT-PCR (qPCR) or ELISA. Data sets were analyzed for standard distribution. If the Shapiro-Wilk test returned a positive result, a t test was performed. The Mann-Whitney Rank Sum test was performed for data without standard distribution. All sick groups were compared to the control group. The data for various diseases outside the udder were combined if a small number of samples had been tested. P values are defined as follows: * $0.05>p>0.01$, and ** p 0.01.

Selection and Evaluation of Potential Biomarkers

The ROC analysis was used to evaluate the discriminatory ability of the biomarkers. An area under the curve (AUC) >0.9 was regarded as highly discriminating and an AUC value<0.6 as non-discriminating. Biomarkers were selected based on the best distinction between minor systemic disease and the control group. Statistical evaluation of biomarkers and marker combinations was performed using TANAGRA open source data mining software. To avoid potential overfitting, cross-validation (CV) was performed (10-fold, 1 repetition). The values for sensitivity, specificity and resubstitution error rate were taken over from the CV. The various diseases were collected into one group. The biomarkers or their combinations were evaluated on the basis of their ability to discriminate sick cows.

Example 1: Differential Gene Expression of Biomarkers in Milk

The mRNA expression of individual biomarkers in milk cells was analyzed with qPCR. To confirm the systemic significance of potential biomarkers from the local environment of the mammary gland, the expression pattern of the biomarkers in peripheral leucocytes was examined. Data from groups with minor and serious systemic diseases was combined and tested in the case of a small number of samples in a systemic disease group. FIG. 1 shows the results for the most relevant biomarkers.

Example 2: Quantification and Selection of Biomarkers

Based on the results of the previous experiments (microarray, qPCR, etc.), potential biomarkers were selected and quantified at the protein level using commercial ELISA kits. Elevated concentrations of IL-18, LTF, PIGR (SC), TNF-alpha and VEGF were detected in milk in the presence of abomasal displacement, serious systemic disease, mastitis and combinations of the diseases. HP and S100A9, however, showed increased values in the presence of minor systemic disease (FIG. 2). The expression patterns of HP, IL-18 and LTF were also confirmed in plasma in order to determine the validity of the markers for systemic diseases. The correlations of milk and plasma HP and LTF concentrations are shown in FIG. 3. The positive Spearman correlation coefficients (Spearman p) show the relationship between milk and plasma protein concentrations. In addition, the correlation of the strongest biomarkers in the milk was examined. All proteins showed positive correlation of concentrations in the milk in the presence of diseases (Table 1). The best markers underwent further statistical evaluation.

TABLE 1

Correlations of Protein biomarkers in milk and plasma

| Correlation of | Spearman correlation coefficient | p | n |
|---|---|---|---|
| Correlation in milk | | | |
| Milk HP and milk PIGR (SC) | 0.67 | 0.001 | 71 |
| Milk LTF and milk PIGR (SC) | 0.61 | 0.001 | 79 |
| Milk HP and milk LTF | 0.59 | 0.001 | 142 |
| Milk HP and milk VEGF | 0.58 | 0.001 | 120 |
| Milk LTF and milk VEGF | 0.54 | 0.001 | 132 |
| Milk VEGF and milk PIGR (SC) | 0.41 | 0.001 | 79 |
| Correlation in milk and plasma | | | |
| Milk HP and plasma HP | 0.78 | 0.001 | 121 |
| Milk IL-18 and plasma IL-18 | 0.38 | 0.088 | 21 |
| Milk LTF and plasma LTF | 0.33 | 0.005 | 69 |
| Correlation in Plasma | | | |
| Plasma HP and plasma LTF | 0.59 | 0.001 | 63 |

Example 3: Statistical Evaluation of the Biomarkers

The heavily regulated and highly concentrated milk biomarkers HP, PIGR (SC), LTF and VEGF were selected for statistical evaluation. A subgroup of samples in which all four markers had been determined was used for a direct comparison of the results.

Figure 4A:
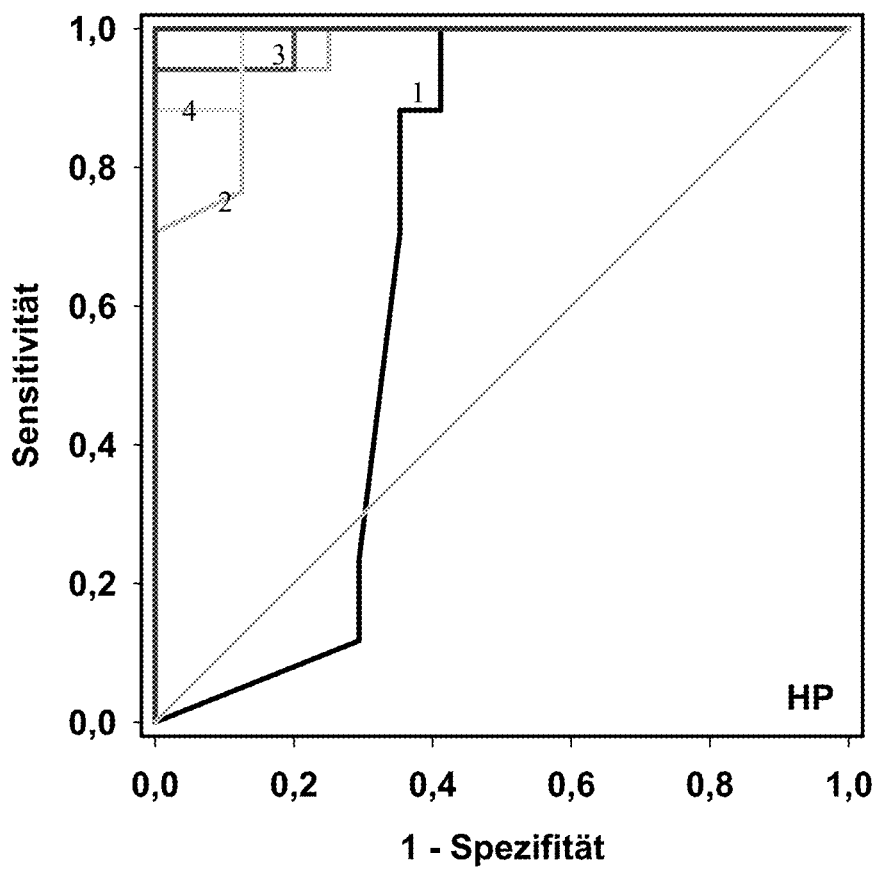
FIG. 4 shows Receiver Operating Characteristics (ROC) curves from selected milk biomarkers.
Figure 4A:
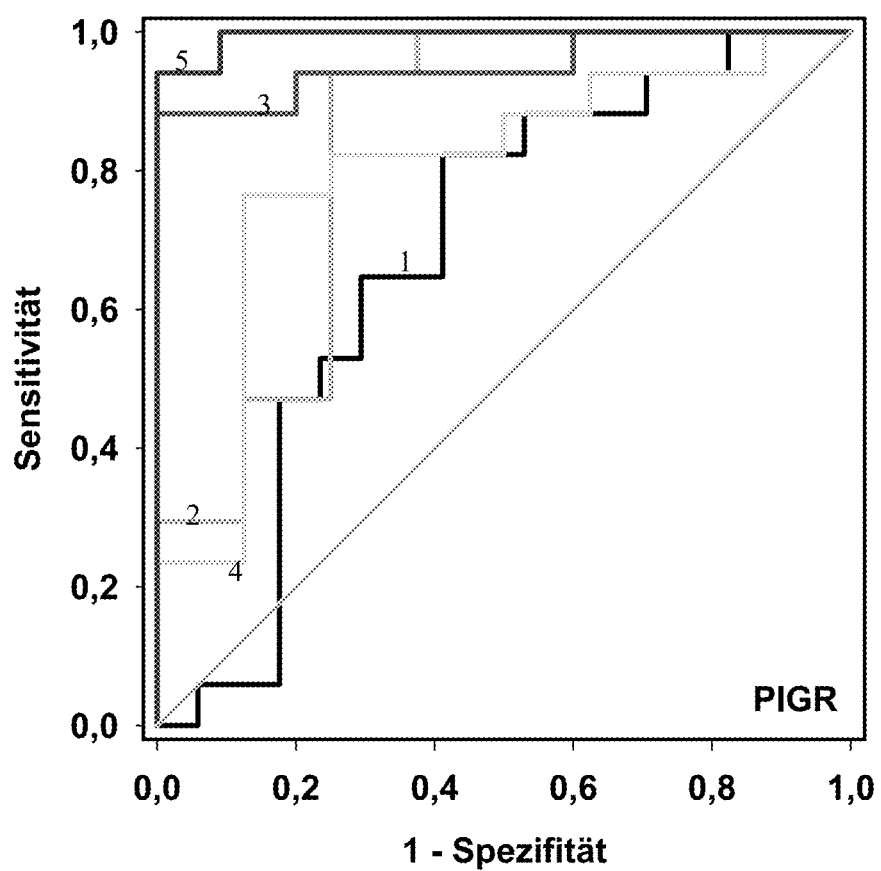
Figure 4A:
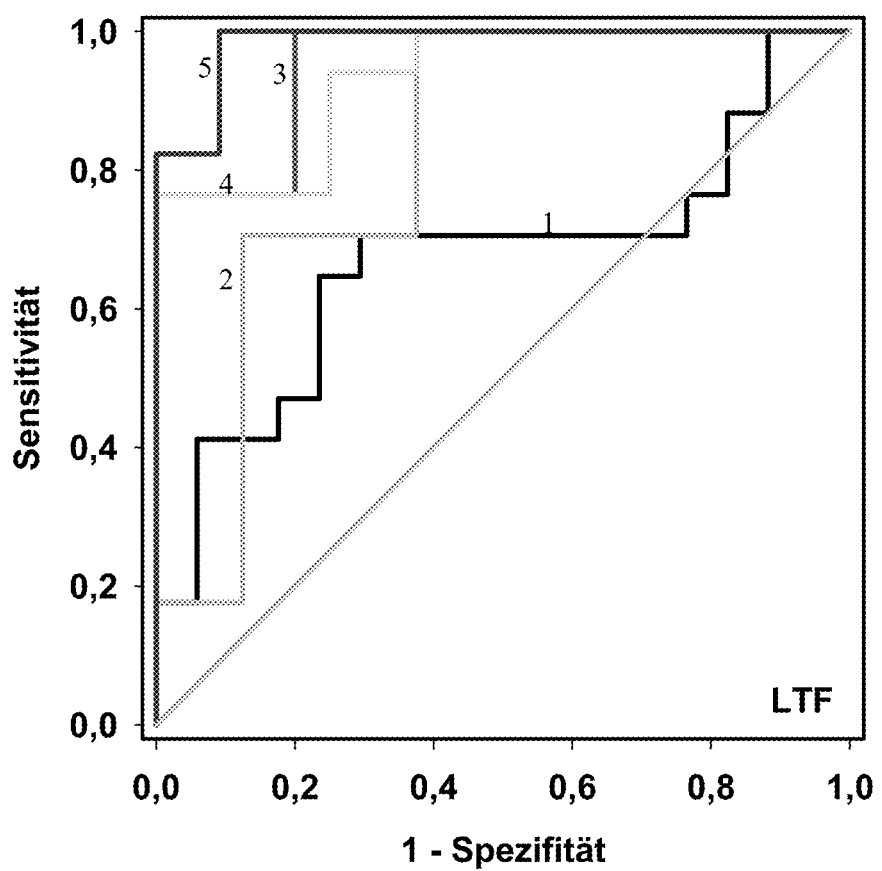
Figure 4A:
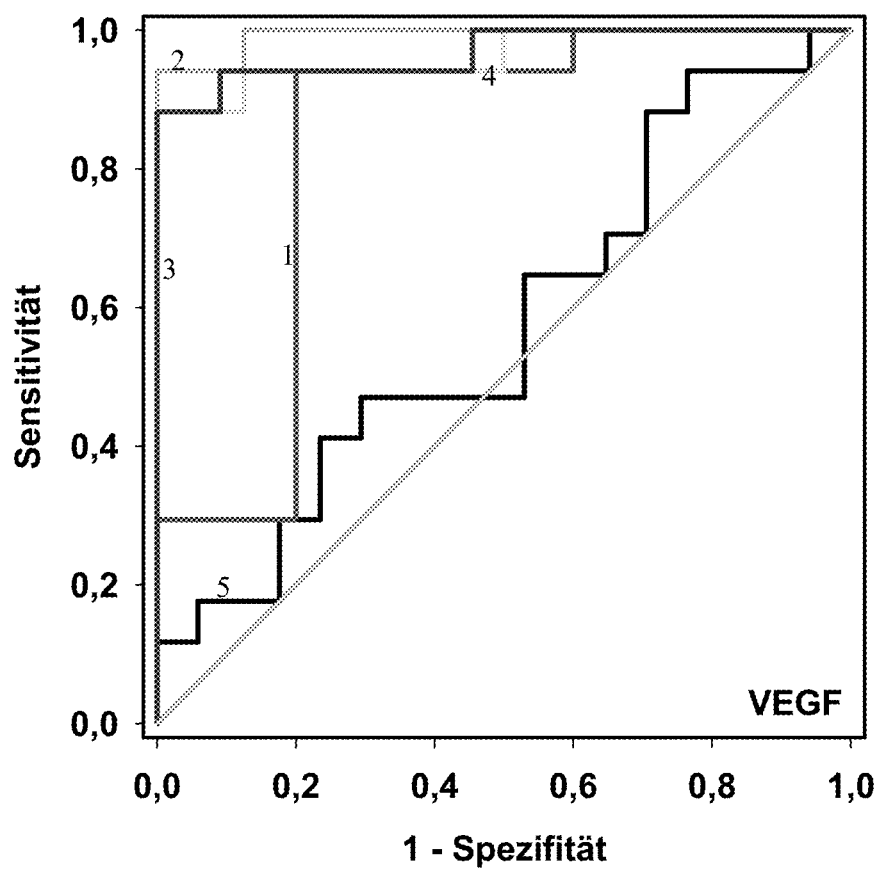

Each biomarker alone and combinations of two biomarkers were evaluated. In this regard, 17 control samples and 49 samples from sick cows were used. The discriminatory ability for each disease group was determined by ROC analysis (FIG. 4A, Table 2). HP and PIGR (SC) showed the best distinction of minor systemic disease with an AUC of 0.69 and 0.68. All proteins were highly discriminating for serious systemic diseases and mastitis (AUC>0.9).

TABLE 2

Discriminatory ability of milk biomarkers for various diseases. The data was generated by means of ROC analysis. (Control: n = 17, minor systemic (system.) disease (Erkrank.): n = 17, Abomasal displacement (LMV) (+metabolic disorder): n = 8, serious systemic disease: n = 5, serious systemic disease + abomasal displacement: n = 8, mastitis: n = 11)

| Control vs. Sick group | AUC | 95% Confidence interval | p |
|---|---|---|---|
| HP | | | |
| Minor systemic disease | 0.69 | 0.48-0.89 | 0.065 |
| LMV (+metabolic disorder) | 0.96 | 0.89-1.03 | <0.001 |
| Serious systemic disease | 0.99 | 0.95-1.03 | 0.001 |
| Serious systemic disease + LMV | 0.99 | 0.95-1.02 | <0.001 |
| Mastitis | 1.00 | 1.00-1.00 | <0.001 |
| PIGR (SC) | | | |
| Minor systemic disease | 0.68 | 0.49-0.87 | 0.071 |
| LMV (+metabolic disorder) | 0.84 | 0.64-1.04 | <0.05 |
| Serious systemic disease | 0.95 | 0.87-1.04 | <0.05 |
| Serious systemic disease + LMV | 0.80 | 0.61-0.99 | <0.05 |
| Mastitis | 0.99 | 0.98-1.01 | <0.001 |
| LTF | | | |
| Minor systemic disease | 0.67 | 0.48-0.86 | 0.088 |
| LMV (+metabolic disorder) | 0.82 | 0.62-1.03 | <0.05 |
| Serious systemic disease | 0.95 | 0.86-1.05 | <0.05 |
| Serious systemic disease + LMV | 0.93 | 0.84-1.03 | <0.001 |
| Mastitis | 0.98 | 0.95-1.02 | <0.001 |
| VEGF | | | |
| Minor systemic disease | 0.57 | 0.38-0.77 | 0.459 |
| LMV (+metabolic disorder) | 0.99 | 0.96-1.02 | <0.001 |
| Serious systemic disease | 0.84 | 0.58-1.08 | <0.05 |
| Serious systemic disease +LMV | 0.96 | 0.90-1.03 | <0.001 |
| Mastitis | 0.97 | 0.91-1.03 | <0.001 |

To discriminate between sick and control animals, marker combinations were evaluated using two statistical classification methods, namely multinomial logistic regression (MLR) and k-nearest neighbor classification (K-NN) (Table 4). A second statistical model was applied to avoid potential distortions of the results. HP is the best choice for use as a single biomarker. In combination with PIGR (SC) or LTF, a minor increase in sensitivity or specificity can be achieved. These combinations showed the best results for detecting sick animals.

Figure 4B:
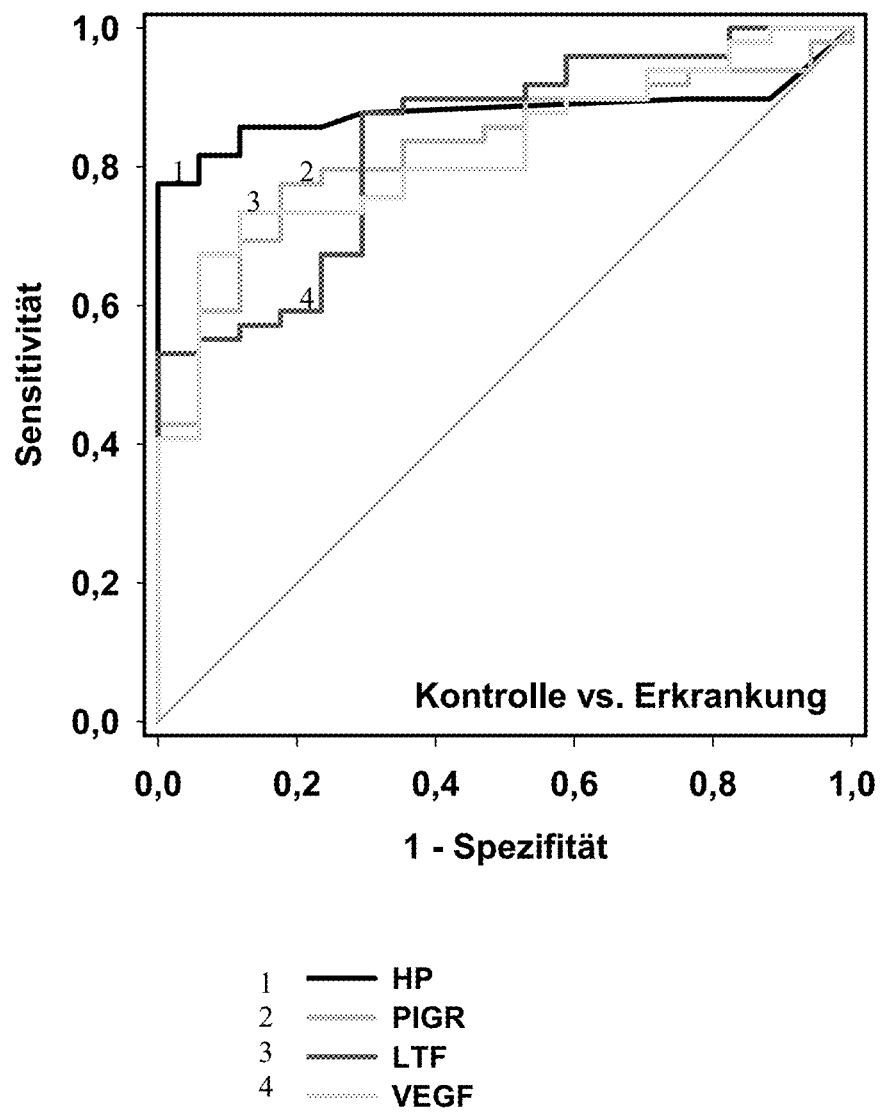
Figure 1:
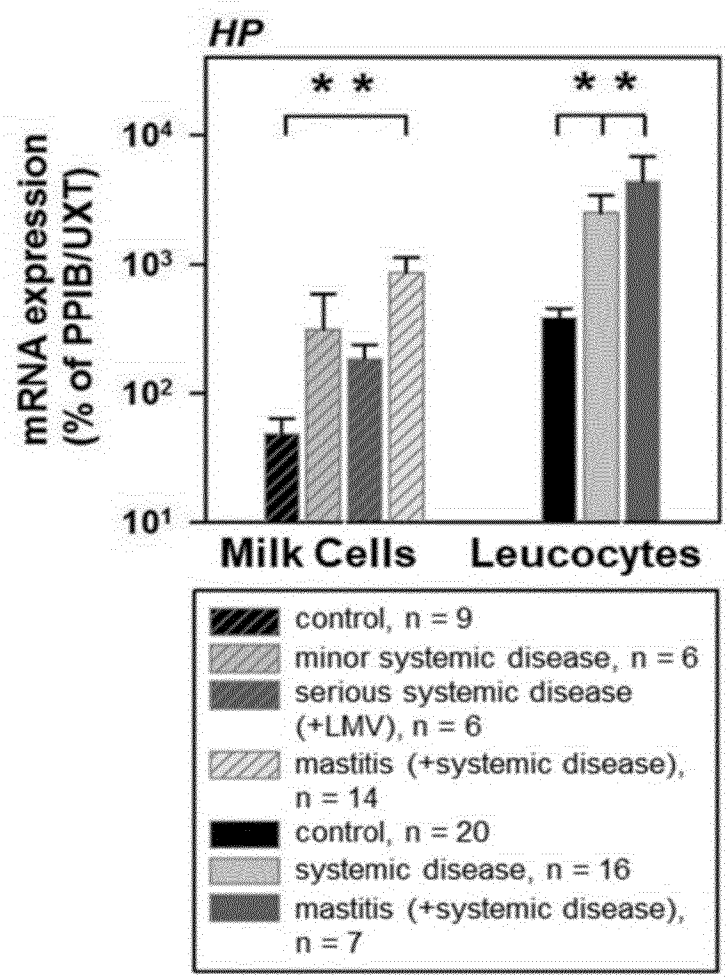
Figure 1:
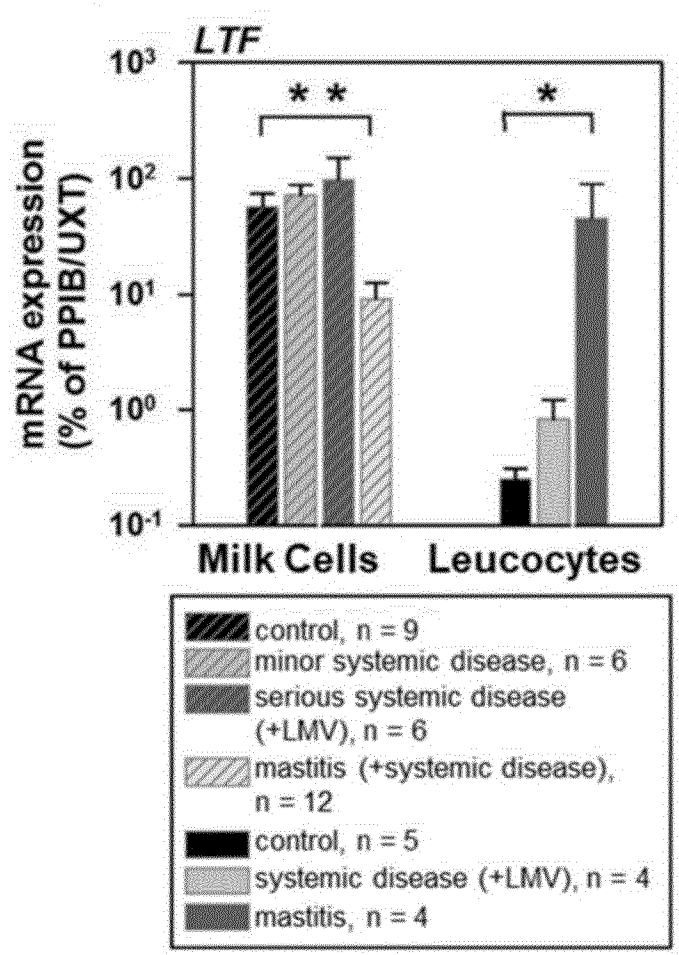
Figure 1:
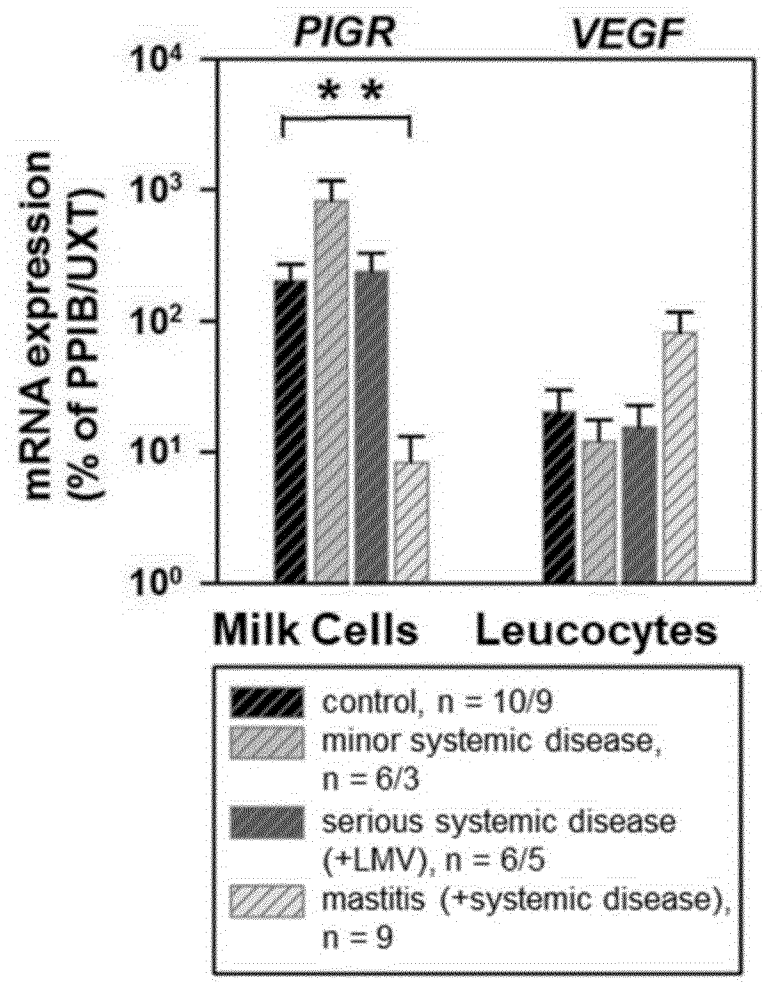
Figure 1:
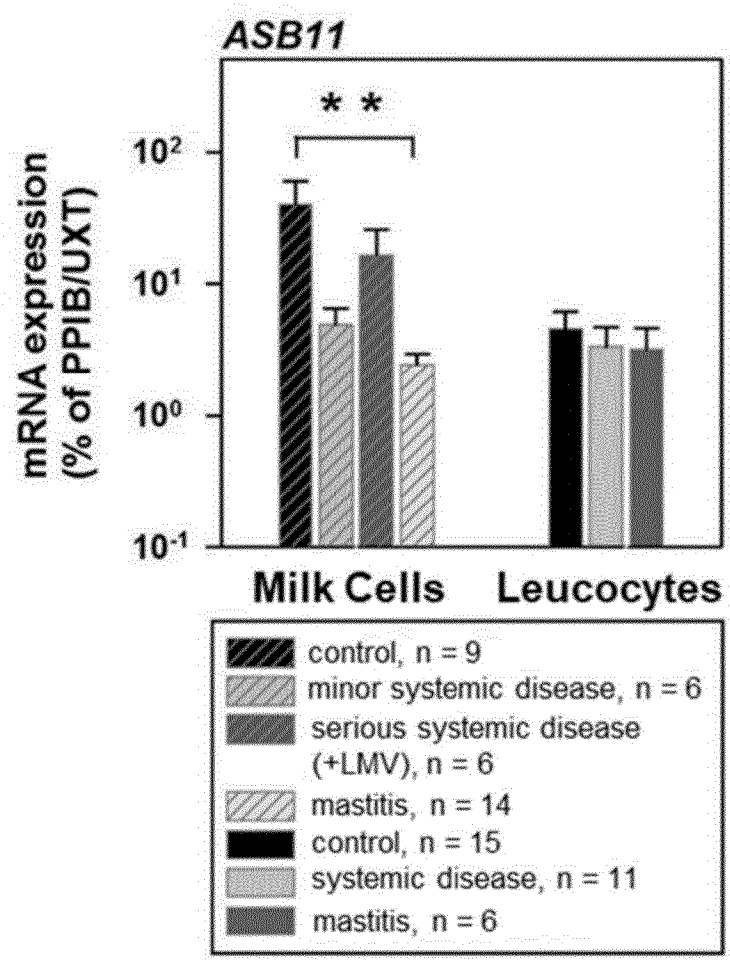
Figure 2:
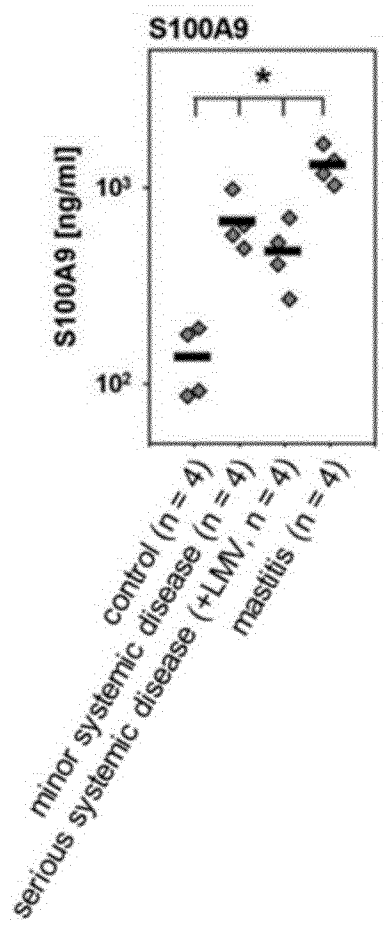
Figure 2:
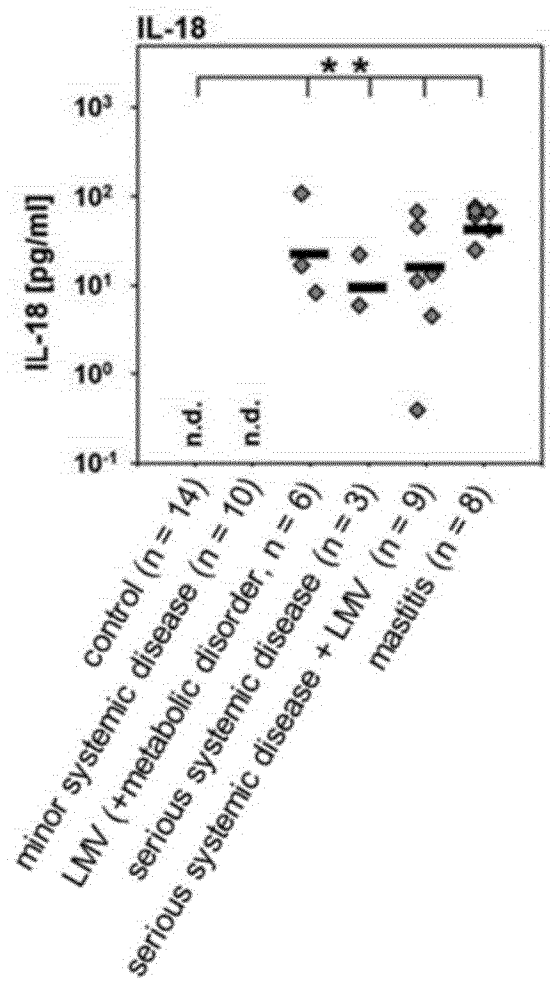
Figure 2:
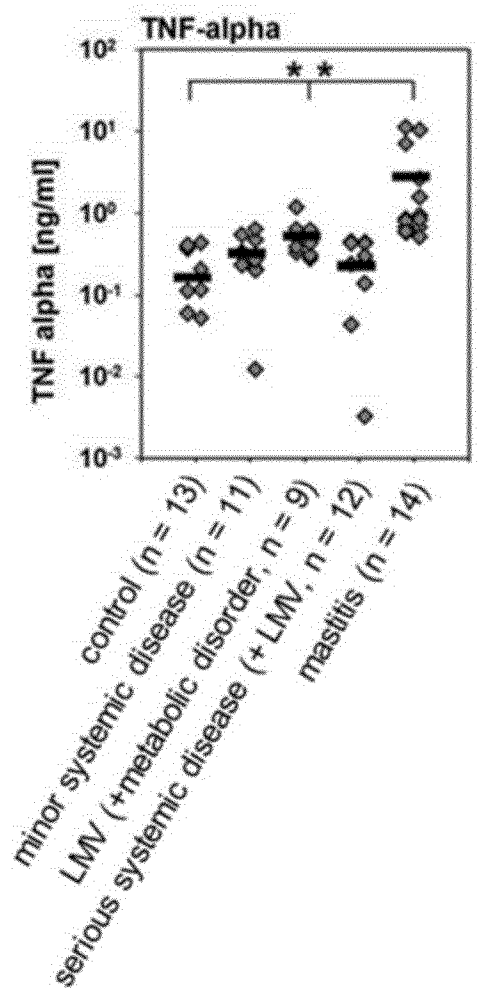
Figure 2:
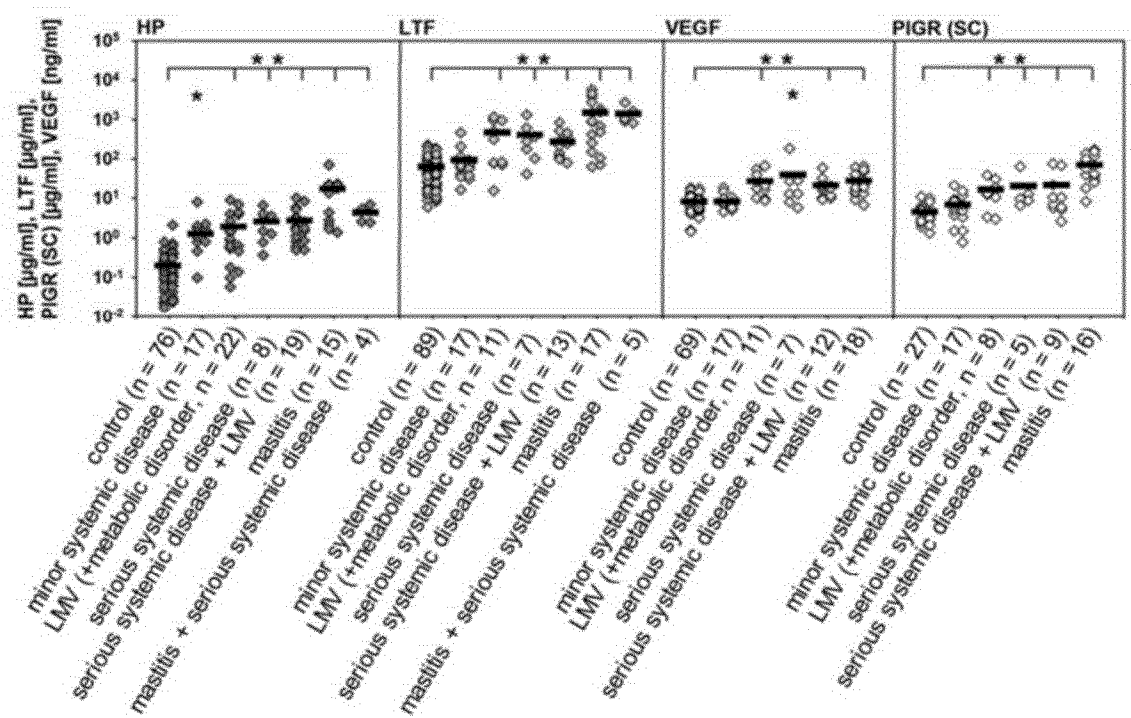
Figure 3:
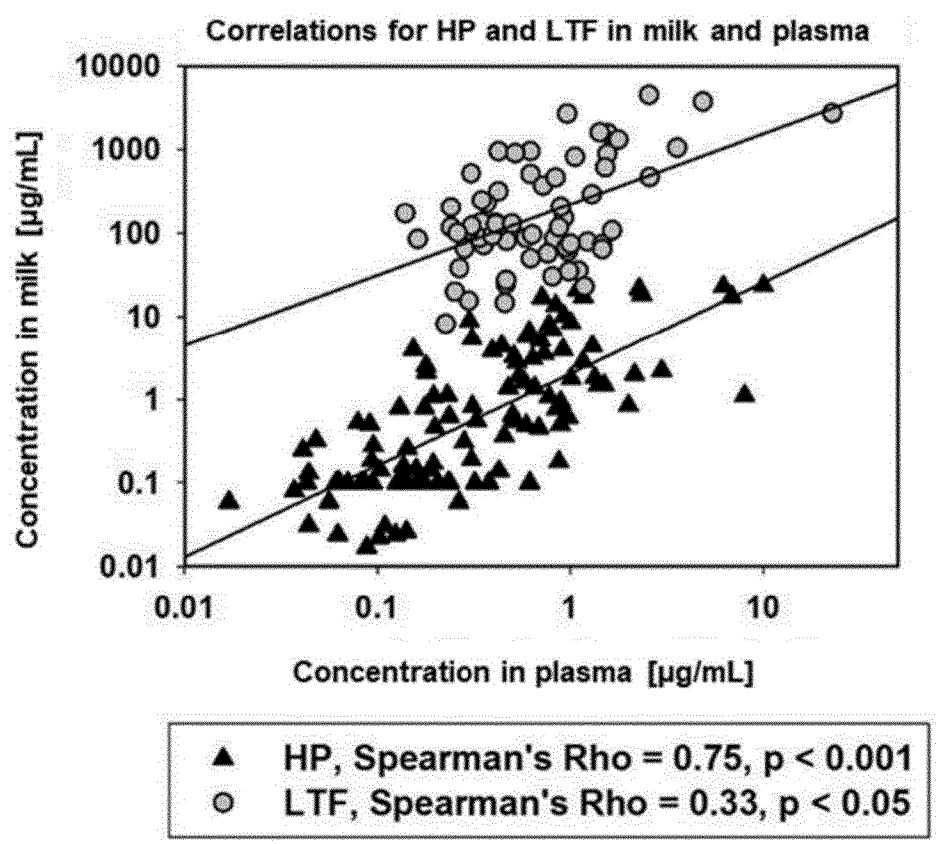
Figure 4A:
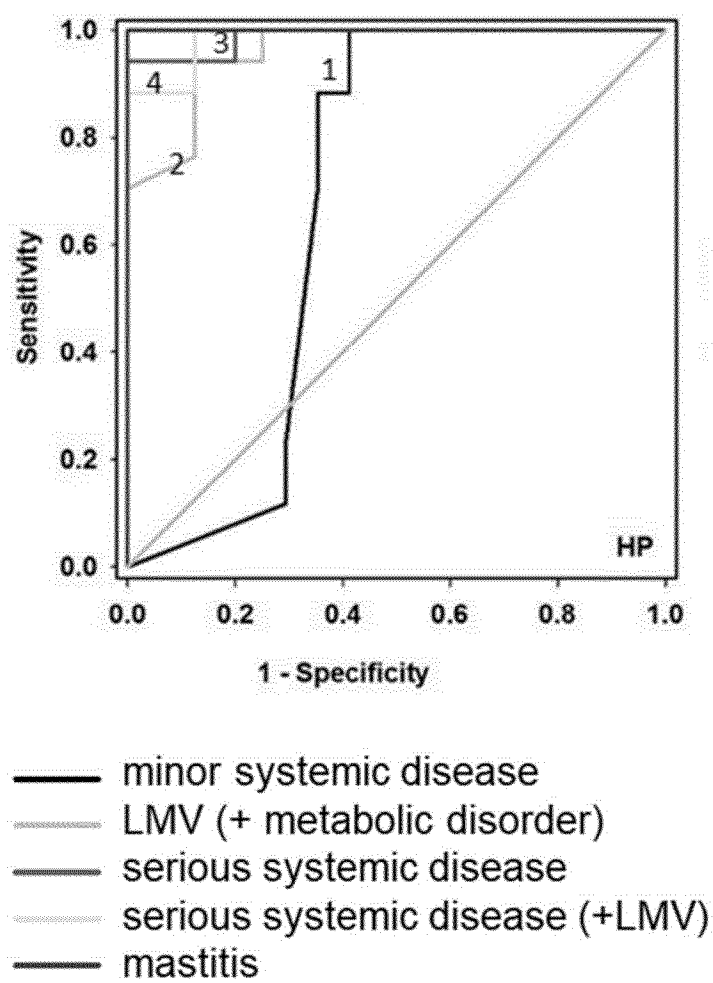
Figure 4A:
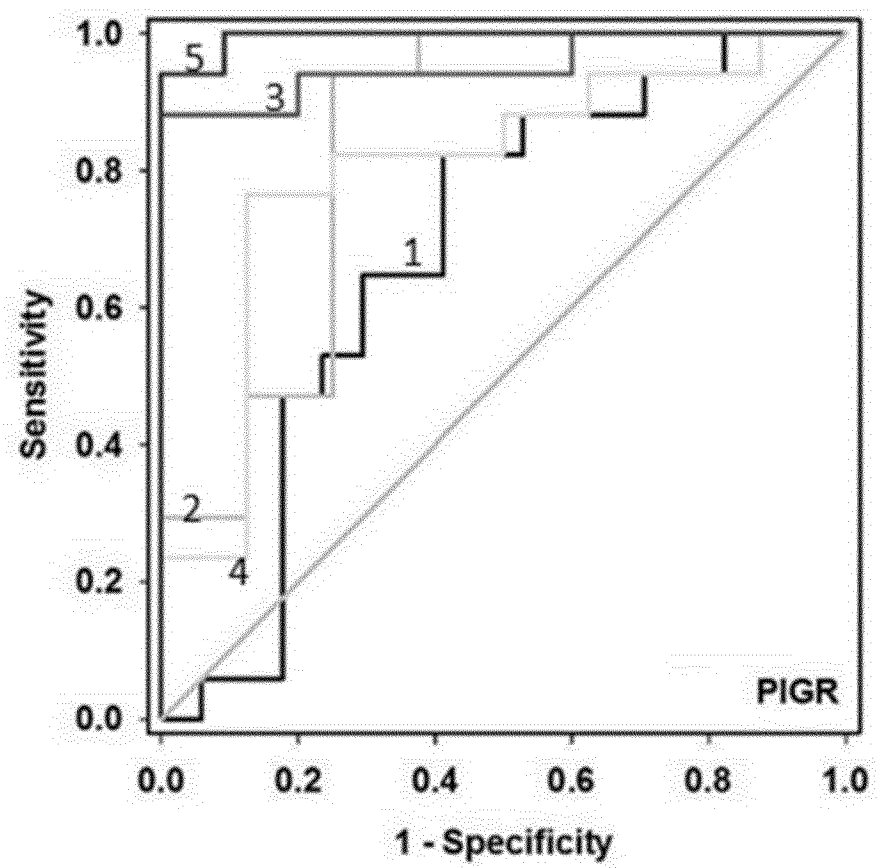
Figure 4A:
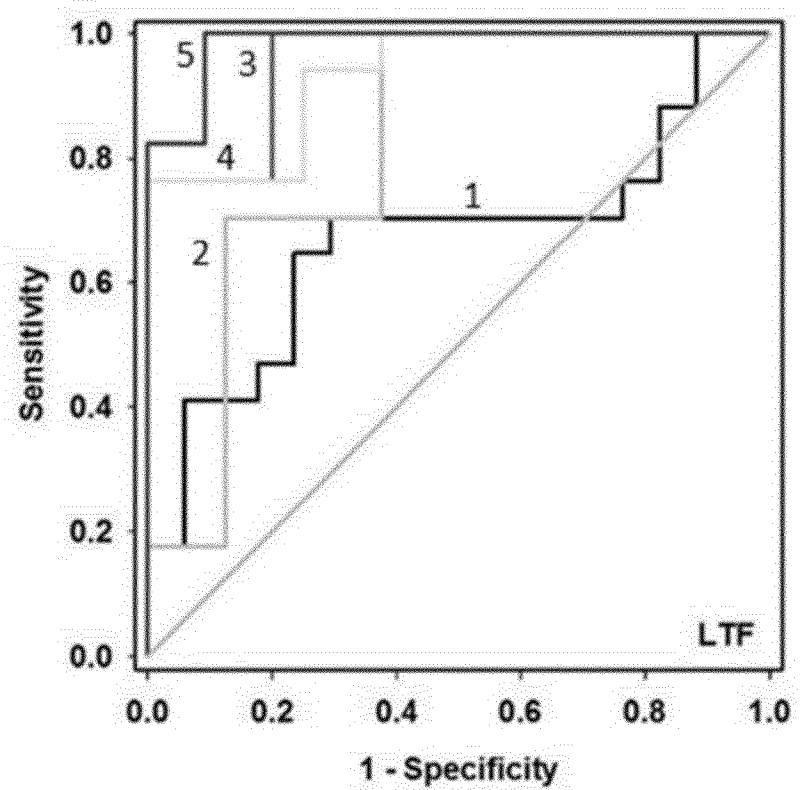
Figure 4A:
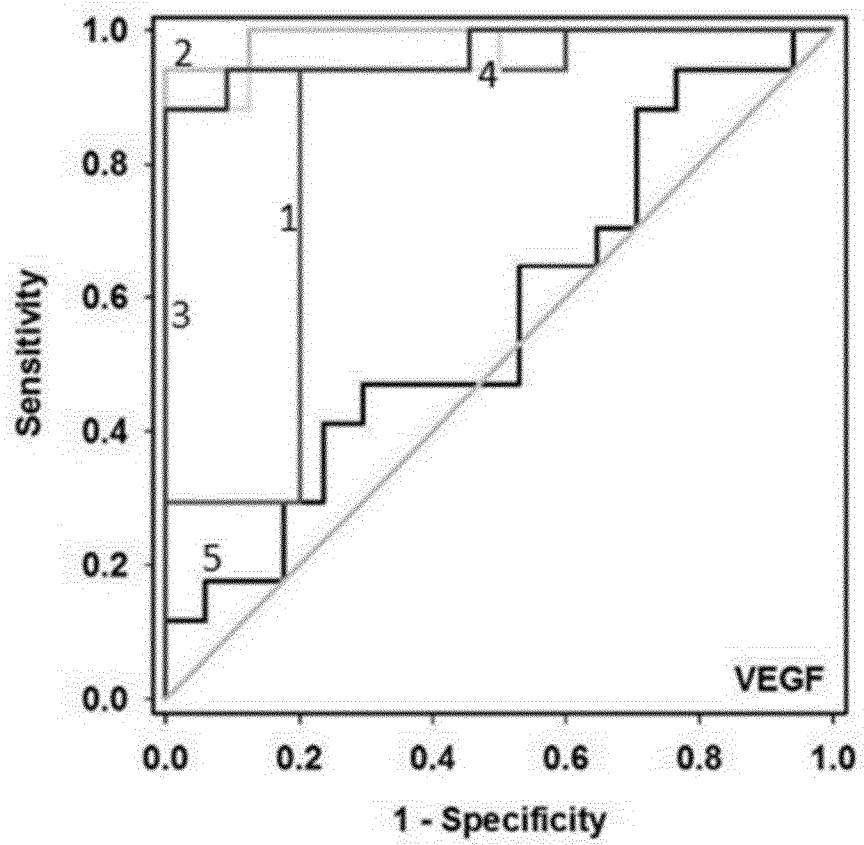
Figure 4B:
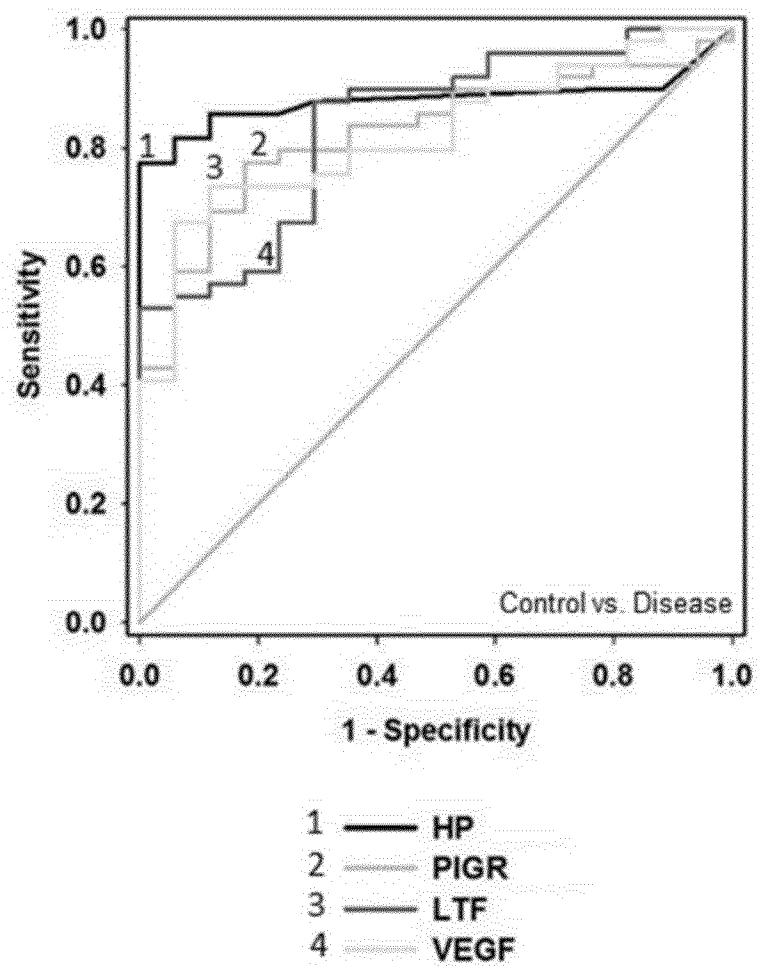

Practical application of biomarkers requires that the tests have high specificity in order not to overestimate the occurrence of diseases in large dairy cattle herds. An ROC analysis was therefore combined for all sick groups vs. control in order to evaluate the sensitivity ("correct positive"), specificity ("correct negative"), 1-sensitivity ("false negative") and 1-specificity ("false positive") of the biomarker determination in milk using various threshold value (cut-off) concentrations. Table 3 shows the values for possible cut-off concentrations with a high specificity of 94%. The corresponding ROC curves are shown in FIG. 4B. At a specificity of 94%, 6% of actually healthy animals would be identified as sick. In the case of determination of HP, PIGR (SC), LTF and VEGF, 18%, 41%, 45% and 33%, respectively, of sick animals would be classified as healthy.

On the basis of this analysis, it could therefore be demonstrated that the determination of HP is suitable for detecting diseases in dairy cattle. A combined measurement with PIGR (SC) or LTF is also possible in order to increase the sensitivity or specificity.

TABLE 3

Discriminatory ability of milk biomarkers for sick animals. The data was generated through ROC analysis. (Control: n = 17, sick: n = 49)

| AUC | 95 % Confidence-interval | P | Cut-Off at 94% specificity | Sensitivity at 94% specificity % |
|---|---|---|---|---|
| HP | | | | |
| 0.88 | 0.80-0.96 | <0.001 | 0.58 µg/ml | 82 |
| PIGR (SC) | | | | |
| 0.82 | 0.72-0.93 | <0.001 | 8.20 µg/ml | 59 |
| LTF | | | | |
| 0.84 | 0.74-0.94 | <0.001 | 120.7 µg/ml | 55 |
| VEGF | | | | |
| 0.82 | 0.72-0.92 | <0.001 | 9.50 ng/ml | 67 |

TABLE 4

Evaluation of milk biomarkers and their combinations. The classification was performed by using MLR and K-NN: Control (n = 17) vs. sick (n = 49). Sensitivity, specificity and resubstitution error rates were taken over from the CV (10-fold, 1 repetition).

| Marker (Combination) | Multinomial logistic regression (cross-validation)/% | | | k-nearest neighbor classification (cross-validation)/% | | |
|---|---|---|---|---|---|---|
| | Sensitivity | Specificity | Error rate | Sensitivity | Specificity | Error rate |
| Single marker | | | | | | |
| HP | 86 | 88 | 13 | 91 | 69 | 15 |
| LTF | 84 | 44 | 27 | 82 | 63 | 23 |
| VEGF | 84 | 38 | 28 | 73 | 31 | 38 |
| PIGR (SC) | 86 | 25 | 30 | 77 | 19 | 38 |
| Marker combinations | | | | | | |
| HP & VEGF | 86 | 88 | 13 | 80 | 94 | 17 |
| HP & PIGR (SC) | 89 | 81 | 13 | 84 | 75 | 18 |
| HP & LTF | 89 | 69 | 17 | 86 | 81 | 15 |
| VEGF & PIGR (SC) | 86 | 63 | 20 | 82 | 56 | 25 |
| LTF & PIGR (SC) | 84 | 56 | 23 | 86 | 31 | 28 |
| LTF & VEGF | 82 | 56 | 25 | 84 | 44 | 27 |

List of Abbreviations

AUC Area Under the Curve
BL Leucocytes
CIA Chemiluminescent immunoassay
CV Cross-validation
EIA Enzyme immunoassay
ELISA Enzyme-linked Immunosorbent Assay
Erkrank. Disease
ESI Electrospray Ionization
FIA Fluorescence immunoassay
FPLC Fast Protein Liquid Chromatography
HP Haptoglobin
HPLC High Performance Liquid Chromatography
Ig Immunoglobulin
IL Interleukin
K-NN k-nearest neighbor classification
LMV Abomasal displacement
LTF Lactoferrin
MALDI Matrix-assisted Laser Desorption/Ionization
MLR Multinomial logistic regression
mRNA Messenger ribonucleic acid
MZ Milk cells
PIGR Polymeric immunoglobulin receptor
PPIB Cyclophilin B (reference gene)
RIA Radio immunoassay
ROC Receiver Operating Characteristic
S100A9 S100 calcium-binding protein A9
SC Secretory Component, secretory component of the PIGR
SDS-PAGE Sodium dodecyl sulfate polyacrylamide gel electrophoresis
SPR Surface plasmon resonance
system. Systemic
TNF-alpha Tumor necrosis factor alpha
UXT Ubiquitously-Expressed Transcript (reference gene)
VEGF Vascular Endothelial Growth Factor

The invention claimed is:

1. A non-invasive system for monitoring the state of health of a dairy cow, comprising:
a means to measure concentrations of two biomarkers including consisting of haptoglobin (HP) and polymeric immunoglobulin receptor (PIGR) in a milk sample, wherein the means to measure the concentrations of the two biomarkers comprises an antibody specific to HP and an antibody specific to PIGR, and
a processor configured to compare the measured concentrations of the two biomarkers with reference values for the two biomarkers, wherein a deviation of the measured concentration from the reference values indicates an unhealthy condition in the dairy cow; and an automated or semi-automated milking system configured to obtain the milk sample from the dairy cow during a milking process.

2. The non-invasive system according to claim 1, further comprising at least one of: a memory and a display.

\* \* \* \* \*

UNITED STATES PATENT AND TRADEMARK OFFICE
CERTIFICATE OF CORRECTION

PATENT NO. : 10,866,250 B2
APPLICATION NO. : 15/580983
DATED : December 15, 2020
INVENTOR(S) : Lehmann et al.

It is certified that error appears in the above-identified patent and that said Letters Patent is hereby corrected as shown below:

In the Drawings

Delete Figures 1 through 4, and insert Figures 1 through 4 from the following pages:

Signed and Sealed this
Twenty-second Day of March, 2022

Drew Hirshfeld
*Performing the Functions and Duties of the
Under Secretary of Commerce for Intellectual Property and
Director of the United States Patent and Trademark Office*

1 —— minor systemic disease
2 —— LMV (+ metabolic disorder)
3 —— serious systemic disease
4 —— serious systemic disease (+LMV)
5 —— mastitis